United States Patent
Chou et al.

(10) Patent No.: US 11,692,927 B2
(45) Date of Patent: Jul. 4, 2023

(54) APPARATUS AND METHODS FOR RAPID DETECTION OF ACUTE PHASE REACTANTS AND WHITE BLOOD CELLS

(71) Applicant: Essenlix Corporation, Monmouth Junction, NJ (US)

(72) Inventors: Stephen Y. Chou, Princeton, NJ (US); Wei Ding, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/295,562

(22) PCT Filed: Nov. 20, 2019

(86) PCT No.: PCT/US2019/062510
§ 371 (c)(1),
(2) Date: May 20, 2021

(87) PCT Pub. No.: WO2020/106909
PCT Pub. Date: May 28, 2020

(65) Prior Publication Data
US 2021/0356382 A1    Nov. 18, 2021

Related U.S. Application Data

(60) Provisional application No. 62/769,977, filed on Nov. 20, 2018.

(51) Int. Cl.
*G01N 33/543* (2006.01)
*G01N 15/14* (2006.01)
(Continued)

(52) U.S. Cl.
CPC ... *G01N 15/1463* (2013.01); *G01N 33/54306* (2013.01); *G01N 2015/008* (2013.01);
(Continued)

(58) Field of Classification Search
None
See application file for complete search history.

(56) References Cited

U.S. PATENT DOCUMENTS

| 2010/0216248 | A1 | 8/2010 | Wardlaw | |
| 2012/0321518 | A1* | 12/2012 | Ermantraut | C12Q 1/6834 422/69 |
| 2013/0302828 | A1* | 11/2013 | Takeda | G01N 21/6428 435/7.23 |

FOREIGN PATENT DOCUMENTS

| EP | 0961110 A2 | 12/1999 |
| JP | 2018059935 A | 4/2018 |

(Continued)

OTHER PUBLICATIONS

Written Opinion of the International Searching Authority for PCT/US19/62510 established by the ISA/KR completed on Mar. 13, 2020.
(Continued)

*Primary Examiner* — Rebecca M Giere

(57) ABSTRACT

The present invention provides diagnostic devices and methods for quantifying the amounts of an acute phase reactant (e.g., C-reactive protein (CRP) or serum amyloid A (SAA)) in a body fluid sample and/or white blood cell counts in blood sample. In particular, the present invention provides a rapid assay to detect CRP, SAA, and/or white blood cells in blood with high sensitivity and specificity.

48 Claims, 14 Drawing Sheets

(51) Int. Cl.
*G01N 15/00* (2006.01)
*G01N 15/10* (2006.01)

(52) U.S. Cl.
CPC ................ *G01N 2015/0038* (2013.01); *G01N 2015/1006* (2013.01); *G01N 2015/1486* (2013.01); *G01N 2333/4737* (2013.01)

(56) References Cited

FOREIGN PATENT DOCUMENTS

| WO | 2017027643 A1 | 2/2017 |
|---|---|---|
| WO | 2017048871 A1 | 3/2017 |
| WO | 2019148054 A1 | 8/2019 |

OTHER PUBLICATIONS

International Preliminary Report on Patentability for PCT/US19/62510 established by IPEA/US completed on Jan. 8, 2021.

* cited by examiner

APPARATUS AND METHODS FOR RAPID DETECTION OF ACUTE PHASE REACTANTS AND WHITE BLOOD CELLS

CROSS-REFERENCE TO RELATED APPLICATIONS

This application is a National Stage entry (§ 371) application of International Application No. PCT/US2019/062510, filed on Nov. 20, 2019, which claims the benefit of priority of U.S. Provisional Patent Application No. 62/769,977, filed Nov. 20, 2018, and is incorporated by reference in its entirety. The entire disclosure of any publication or patent document mentioned herein is entirely incorporated by reference.

FIELD

Among other things, the present invention is related to devices and methods of performing biological and chemical assays, such as immunoassays.

BACKGROUND

Acute phase reactants (APRs) have traditionally been used as biomarkers for inflammation and as a measure of "sickness index" during infectious. There are numerous ARPs including C-reactive protein (CRP), mannose-binding protein, complement factors, ferritin, ceruloplasmin, serum amyloid A, haptoglobin, and the like. CRP, an acute phase reactant, produced mainly in liver, is generally known as a biomarker of inflammation. CRP is considered as a specific biomarker for bacterial infection, because viral infections do not lead to CRP production from the liver cells. In addition, CRP can be used in differentiating inflammatory diseases (e.g., inflammatory bowel disease, intestinal lymphoma, or intestinal tuberculosis). Serum amyloid A (SAA) represents another exemplary acute phase reactant. SAA is enriched in the native, high-density lipoprotein (HDL) in human serum. Bacterial infection often leads to an increase in WBCs in blood. Detecting and measuring acute phase reactants (e.g., CRP and SAA) and WBC are useful in determining disease progress or the effectiveness of treatments. Current methodology of acute phase reactants and WBC measurement includes ELISA, immunoturbidimetry, nephelometry, rapid immunodiffusion, visual agglutination, hemocytometer, and flow cytometry. Although many immunoassays to detect acute phase reactants (e.g., CRP or SAA) in the blood are known, there remains a need for rapid and sensitive assays to accurately detect the presence of acute phase reactants in a body fluid sample and, if present, to quantitate its presence. There is also a need to measure white blood cells and corresponding acute phase reactant levels during infections.

SUMMARY

The present invention relates to diagnostic devices and methods useful in rapid detection and quantification of the amount of acute phase reactions such as C-reactive protein (CRP), serum amyloid A (SAA) and/or white blood cells (WBC) present in a body fluid sample such as blood. In addition, the present invention relates to methods for making such devices.

In one aspect, the present invention provides an apparatus for measuring a first analyte and a second analyte in a blood sample, comprising: (a) a first plate; (b) a second plate; (c) a plurality of spacers fixed to at least one of the first plate and the second plate; and (d) a sample contact area disposed on at least one of the first plate and the second plate; wherein said plurality of spacers having: (i) a pillar shape; (ii) a substantially flat top surface, (iii) a substantially uniform height, and (iv) a constant inter-spacer distance, wherein the sample contact area is configured to hold a blood sample that contains or is suspected to contain a first analyte and a second analyte, and wherein the sample contact area comprises: (i) a capture reagent immobilized on the sample contact area, wherein the capture reagent is configured to bind to the first analyte to form a complex, (ii) a detection reagent immobilized on the sample contact area, wherein the detection reagent is configured to be diffusible in the sample and bind to the complex, and (iii) a staining reagent immobilized on the sample contact area, wherein the staining reagent is configured to stain the second analyte. In some embodiments, the first analyte is an acute phase reactant. More In some embodiments, the acute phase reactant is at least one compound selected from CRP or SAA. In some embodiments, the second analyte is WBC. In some embodiments, the one or both of the plates having a plurality of spacers. The spacers have a substantially uniform height of 5 to 30 µm. In some embodiments, the spacers have a substantially uniform height of 10 µm. In some embodiments, the capture reagent is an antibody or an aptamer. The antibody can be a monoclonal antibody or polyclonal antibody. In some embodiments, the monoclonal antibody binds to CRP or SAA. In some embodiments, the antibody is conjugated to a microstructure that is immobilized on the sample contact area. The microstructure can be a plurality of beads. In some embodiments, the plurality of beads is made of polystyrene or silica. In some embodiments, the plurality of beads has a diameter of 2 to 30 µm. More In some embodiments, the plurality of beads has a diameter of 10 µm. In some embodiments, the detection reagent is an antibody. The antibody can be a monoclonal antibody or a polyclonal antibody. In some embodiments, the monoclonal antibody binds to a complex of the capture reagent and CRP or a complex of the capture reagent and SAA.

In some embodiments, the detection reagent is labeled with a fluorescence. The fluorescence can be FITC, rhodamine, or Cy5. The staining reagent can be SYTO 9. In some embodiments, the apparatus can further comprise a protein stabilizer immobilized on the sample holder. In some embodiments, the apparatus can further comprise a mobile device, wherein said mobile device comprising an imager is configured to capture images of the sample. In some embodiments, the apparatus further comprising an adaptor, wherein the adaptor is configured to accommodate the sample holder and to position the sample in a field of view (FOV) of the imager when the adaptor is attached to the mobile device and be attachable to a mobile device. In some embodiments, the adaptor has a light source capable of emitting a light with a wavelength of 400 to 700 nm. More In some embodiments, the adaptor has a light source capable of emitting a light with a wavelength of 650 nm. More In some embodiments, the adaptor has a light source capable of emitting a light with a wavelength of 450 nm. In some embodiments, the mobile device is an iPhone. More In some embodiments, the iPhone is iPhone 6S or iPhone 10. In another aspect, the present invention provides an apparatus for measuring a first analyte and a second analyte in a blood sample, comprising: (a) a first plate; (b) a second plate; (c) a plurality of spacers fixed to at least one of the first plate and the second plate; and (d) a sample contact area disposed on at least one of the first plate and the second plate; wherein said plurality of spacers having (i) a pillar shape; (ii) a substantially flat top surface, (iii) a substantially uniform height, and (iv) a constant inter-spacer distance, and wherein the sample contact area is configured to hold a blood sample that contains or is suspected to contain a first analyte and a second analyte, and said sample contact area comprising: (i) a first capture reagent immobilized on the sample contact area, wherein the first capture reagent is configured to bind to the first analyte to form a first complex, (ii) a first detection reagent immobilized on the sample contact area, wherein the detection reagent is configured to be diffusible in the sample and bind to the first complex, (iii) a second capture reagent immobilized on the sample contact area, wherein the second capture reagent is configured to bind to the second analyte to form a second complex, and (iv) a second detection reagent immobilized in the sample contact area, wherein the second detection reagent is configured to be diffusible in the sample and bind to the second complex. In some embodiments, the first analyte is CRP. In some embodiments, the second analyte is SAA. More In some embodiments, the first analyte is CRP and the second analyte is SAA. In some embodiments, one or both of the plates having a plurality of spacers. The spacers have a substantially uniform height of 5 to 30 µm. In some embodiments, the plurality of spacers has a substantially uniform height of 10 µm. In some embodiments, the first capture reagent is an antibody or an aptamer. The antibody is a monoclonal antibody. In some embodiments, the monoclonal antibody binds to CRP. In some embodiments, the second capture reagent is an antibody or an aptamer. The antibody is a monoclonal antibody. In some embodiments, the monoclonal antibody binds to SAA. In some embodiments, the antibody is conjugated to a microstructure that is immobilized on the sample contact area. In some embodiments, the microstructure is a plurality of beads. In some embodiments, the plurality of beads is made of polystyrene or silica. In some embodiments, the plurality of bead has a diameter of 2 to 30 µm. More In some embodiments, the plurality of bead has a diameter of 10 µm. In some embodiments, the first detection reagent is an antibody. In some embodiments, the antibody is a monoclonal antibody. In some embodiments, the monoclonal antibody can bind to a first complex of the first capture reagent and CRP. In some embodiments, the second detection reagent is a monoclonal antibody. In some embodiments, the monoclonal antibody binds to a second complex of the second capture reagent and SAA. In some embodiments, the second detection reagent is labeled with a fluorescence. In some embodiments, the fluorescent label can be, for example, FITC, rhodamine, or Cy5. In some embodiments, the apparatus further comprises a mobile device, wherein said mobile device comprising an imager is configured to capture images of the sample.

In some embodiments, the apparatus further comprises an adaptor, wherein the adaptor is configured to accommodate the sample holder and to position the sample in a field of view (FOV) of the imager when the adaptor is attached to the mobile device and attached to a mobile device, In some embodiments, the adaptor has a light source capable of emitting a light with a wavelength of 400 to 700 nm. In some embodiments, the adaptor has a light source capable of emitting a light with a wavelength of 650 nm. In some embodiments, the adaptor has a light source capable of emitting a light with a wavelength of 450 nm. In some embodiments, the mobile device is an iPhone. More In some embodiments, the iPhone is an iPhone 6S or an iPhone 10. In another aspect, the present invention provides a method for measuring an acute phase reactant and white blood cells (WBC) in a blood sample, comprising: (a) providing a blood sample from a subject, said blood sample contains or is suspected to contain an acute phase reactant and WBC; (b) providing a device comprising a first plate and a second plate, one or both of the plates having: (i) a sample contact area on its respective inner surface configured to contact the blood sample, (ii) a plurality of spacers fixed on at least one of the first plate and the second plate, (iii) a capture reagent for the acute phase reactant, wherein the capture reagent is conjugated to a microstructure that is immobilized on the sample contact area and is configured to bind to the acute phase reactant to form a complex, (iv) a fluorescently labeled detection reagent for the acute phase reactant, wherein the fluorescent labeled detection reagent is immobilized on the sample contact area and is configured to be diffusible in the sample and bind to the complex and generate a first fluorescent signal, and (v) a staining reagent for the WBC, wherein the staining reagent is immobilized on the sample contact area and is configured to stain the WBC to generate a second fluorescent signal; (c) depositing the blood sample on the sample contact area; (d) pressing the first plate and the second plate to compress the sample into a thin layer; (e) incubating the pressed plates for a time period sufficient to allow the generation of the first fluorescent signal and the second fluorescent signal; and (f) measuring the CRP and the WBC by imaging and analyzing the first fluorescent signal and the second fluorescent signal, respectively. In some embodiments, the subject is a human. In some embodiments, the subject is a dog or a cat.

In some embodiments, the acute phase reactant is C-reactive protein (CRP) or serum amyloid A (SAA). More In some embodiments, the acute phase reactant is C-reactive protein. More In some embodiments, the acute phase reactant is serum amyloid A (SAA). In some embodiments, the device is a QMAX card. In some embodiments, the sample contact area is on the first plate. In some embodiments, the plurality of spacers has a uniform height of 5 to 30 µm. More In some embodiments, the plurality of spacers has a uniform height of 10 µm. In some embodiments, the plurality of spacers is on the first plate. In some embodiments, the capture reagent is an antibody. In some embodiments, the antibody is a monoclonal antibody. In some embodiments, the monoclonal antibody is an anti-CRP monoclonal antibody. In some embodiments, the monoclonal antibody is an anti-SAA monoclonal antibody. In some embodiments, the capture reagent for CRP or SAA is on the first plate. In some embodiments, the detection reagent is an antibody. In some embodiments, the antibody is a monoclonal antibody. More In some embodiments, the monoclonal antibody is labeled with a fluorescence. The fluorescence can be FITC, rhodamine, or Cy5. In some embodiments, the monoclonal antibody is CY5-labeled. In some embodiments, the fluorescent-labeled antibody is on the second plate. In some embodiments, the staining reagent is on the first plate. In some embodiments, the staining reagent is SYTO 9. In some embodiments, the microstructure is a plurality of beads. In some embodiments, the bead is made of polystyrene or silica. In some embodiments, the plurality of beads has a diameter of 2 to 30 µm. More In some embodiments, the plurality of beads has a diameter of 10 µm. In some embodiments, the time period is about 15 seconds to about 60 seconds. More In some embodiments, the time period is about 60 seconds. In one aspect, the present invention provides a method for measuring C-reactive protein (CRP) and white blood cells (WBC) in a blood sample, comprising: (a) obtaining a first plate and a second plate, wherein each plate comprises: (i) on its respective inner surface, a sample contact area that is configured to contact a liquid sample, wherein an antibody to CRP is conjugated to a plurality of beads that are immobilized on the sample contact area of one or both of the plates, (ii) a labeling anti-CRP capture antibody is immobilized on the sample contact area, (iii) a fluorescent-labeled detection antibody configured to be diffusible in the sample and bind to a complex of the capture antibody and the CRP, (iv) a staining reagent for WBC, wherein the plates are moveable relative to each other in different configurations, including an open configuration and a closed configuration, wherein in the open configuration, the plates are partly or entirely separated apart with an average gap of more than 300 μm between the plates, and in the closed configuration, the plates are pressed against each other with a gap of less than 200 μm between the plates; (b) depositing the sample in the sample contact area when the plates are in the open configuration, wherein the blood sample contains or is suspected to contain CRP or WBC; (c) changing the plates into a closed configuration by compressing the sample into a thin layer, which is at least partly confined by the two sample contact areas that face each other; (d) incubating, after step (c), for about 15 seconds to about 60 seconds; and (e) detecting, after step (d), without washing or opening the plates, the CRP and WBC by imaging the sample layer and detecting signals from the fluorescent-labeled detection antibody that binds to the complex of the capture antibody and the CRP and the staining reagent, respectively. In one aspect, the present invention provides a method for measuring serum amyloid A (SAA) and white blood cells (WBC) in a blood sample, comprising: (a) obtaining a first plate and a second plate, wherein each plate comprises: (i) on its respective inner surface, a sample contact area that is configured to contact a liquid sample, wherein an antibody to SAS is conjugated to a plurality of beads that are immobilized on the sample contact area of one or both of the plates, (ii) a labeling anti-SAD capture antibody is immobilized on the sample contact area, (iii) a fluorescent-labeled detection antibody configured to be diffusible in the sample and bind to a complex of the capture antibody and the SAS, (iv) a staining reagent for WBC, wherein the plates are moveable relative to each other in different configurations, including an open configuration and a closed configuration, wherein in the open configuration, the plates are partly or entirely separated apart with an average gap of more than 300 μm between the plates, and in the closed configuration, the plates are pressed against each other with a gap of less than 200 μm between the plates; (b) depositing the sample in the sample contact area when the plates are in the open configuration, wherein the blood sample contains or suspected to contain SAA or WBC; (c) changing the plates into a closed configuration by compressing the sample into a thin layer, which is at least partly confined by the two sample contact areas that face each other; (d) incubating, after step (c), for about 15 to about 60 seconds; and (e) detecting, after step (d), without washing or opening the plates, the SAA and WBC by imaging the sample layer and detecting signals from the fluorescent-labeled detection antibody that binds to the complex of the capture antibody and the SAA and the staining reagent, respectively.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means. In some embodiments of the present invention.

Figure 1:
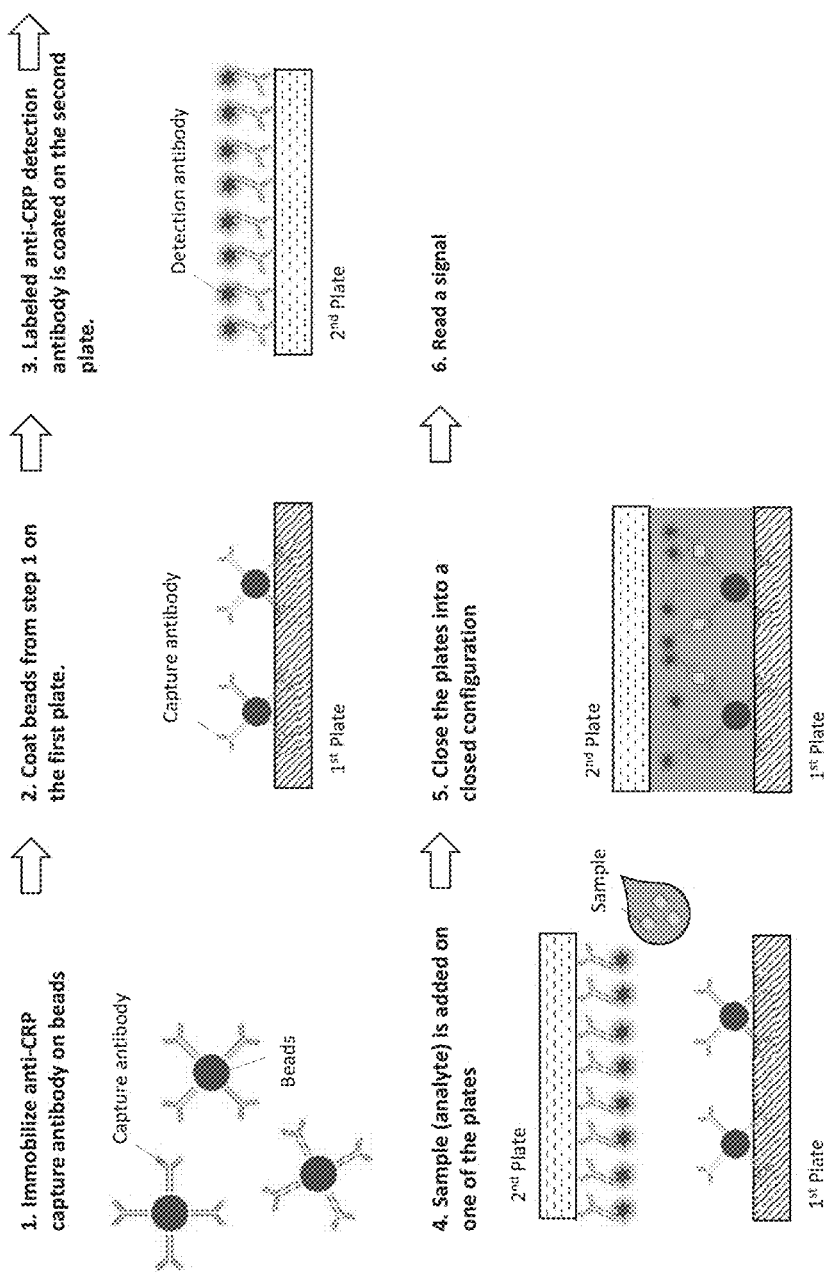
FIG. 1 provides a schematic showing the process for detecting C-Reactive Protein (CRP).

These and other objects, features, and advantages of the present invention will become apparent in light of the detailed description provided below, together with the accompanying drawings.

DETAILED DESCRIPTION

The following description provides some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

It should be noted that the Figures do not intend to show the elements in strict proportion. For clarity purposes, some elements are enlarged when illustrated in the Figures. The dimensions of the elements should be delineated from the descriptions herein provided and incorporated by reference.

Definitions:

The terms "cell" and "targeted cell" are interchangeable.

The term "analyte" and "non-cell analyte" are interchangeable.

The term "QMAX-card" refer to a device that comprises a first plate and a second plate that are movable relative to each other into different configurations (including an open configuration and a closed configuration), and that comprises spacers that regulate the spacing between the plates.

The term "X-plate" refers to one of the two plates in a QMAX-card, wherein the spacers are fixed to this plate. More detailed descriptions of the QMAX-card and X-plate are described in the provisional application Ser. No. 62/456,065, filed on Feb. 7, 2017, which is incorporated herein in its entirety for all purposes.

The term "CROF device" refers to a device that performs a CROF process.

The term "CROF plates" refers to the two plates used in performing a CROF process.

The term "plate" refers to, unless being specified otherwise, the plate used in a CROF process, which a solid that has a surface that can be used, together with another plate, to compress a sample placed between the two plates to reduce a thickness of the sample.

The term "first plate" or "second plate" refers to the plate used in a CROF process.

The term "spacers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e., the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "at most" means "equal to or less than". For example, "a spacer height is at most 1 µm", it means that the spacer height is equal to or less than 1 µm.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing. The present invention provides devices and methods for rapidly detecting two analytes (namely, a first analyte and a second analyte). In certain embodiments, the first analyte is an acute phase reactant. In certain embodiments, the acute phase reactant is C-reactive protein (CRP). In certain embodiments, the acute phase reactant is serum amyloid A (SAA). In certain embodiments, the second analyte is a blood cell component (e.g., white blood cells). In certain embodiments, the first analyte is a first acute phase reactant and the second analyte is a second acute phase reactant (e.g., CRP and SAA). The present invention provides devices and methods of rapidly detecting and quantifying the levels of an acute phase reactant in a blood sample. An advantage of the present invention relates to the simultaneous detection of a first analyte and a second analyte. In certain embodiments, the two analytes are CRP and white blood cells. In certain embodiments, the two analytes are SAA and white blood cells. In certain embodiments, the two analytes are two acute phase reactants such as CRP and SAA. An advantage of the present invention relates to the rapid time for the test. In accordance with the present invention, the test can be performed in about or less than 60 seconds. In some embodiments, the test can be performed in about or less than 30 seconds.

The present invention provides a rapid, reliable and simple test for acute phase reactant in serum protein (as a first analyte) and white blood cells (as a second analyte). The assay can detect an acute phase reactant in a biological sample. An exemplary acute phase reactant is CRP. The present assay provides a rapid detection for CRP in blood, serum or plasma. CRP is an annular, pentameric protein found in blood plasma, whose levels rise in response to inflammation. It is an acute-phase protein of hepatic origin that increases following interleukin-6 secretion by macrophages and T cells. Accordingly, the present assay provides a test to evaluate if a subject has inflammation. The present CRP assay is sensitive and has a limit of detection (LOD) of 30 ng/mL and an accuracy range of 30 ng/mL-22 µg/mL. In healthy adults, the normal concentrations of CRP varies from 0.8 µg/mL to 3.0 µg/mL. In acute inflammation, CRP can raise as much as 500 to 1,000 µg/mL within 4 to 6 hours in mild to moderate inflammation or insult such as skin infection, cystitis, or bronchitis. It can double every 8 hours and reaches its peak at 36 to 50 hours following injury or inflammation. CRP between 1,000 to 5,000 µg/mL is considered as bacterial inflammation. CRP concentrations between 20 to 100 µg/mL are considered as metabolic inflammation (metabolic pathways that causes arteriosclerosis and Type II diabetes mellitus). Once inflammation subsides, CRP level falls quickly because of its short half-life (4 to 7 hours). The present invention also provides a rapid, reliable and simple test for additional acute phase reactant such as serum amyloid A (SAA). The assay can detect SAA in blood, serum or plasma. Different isoforms of SAA are expressed constitutively (constitutive SAAs) at different levels or in response to inflammatory stimuli (acute phase SAAs). These proteins are produced predominantly by the liver. The conservation of these proteins throughout invertebrates and vertebrates suggests that SAAs play a highly essential role in all animals. Acute phase SAAs are implicated in several chronic inflammatory diseases, such as amyloidosis, atherosclerosis, and rheumatoid arthritis. Three acute-phase SAA isoforms have been reported in mice, called SAA1, SAA2, and SAA3. During inflammation, SAA1 and SAA2 are expressed and induced principally in the liver, whereas SAA3 is induced in many distinct tissues. SAA1 and SAA2 genes are regulated in liver cells by the proinflammatory cytokines IL-1, IL-6, and TNF-α. Both SAA1 and SAA2 are induced up to a 1000-fold in mice under acute inflammatory conditions following exposure to bacterial lipopolysaccharide (LPS). Three A-SAA genes have also been identified in humans, although the third gene, SAA3, is believed to represent a pseudogene that does not generate messenger RNA or protein. Molecular weights of the human proteins are estimated at 11.7 kDa for SAA1 and 12.8 kDa for SAA4.

The present assay provides a test to evaluate if a subject has inflammation based on SSA1 and/or SSA2. The present SAA assay is sensitive and has a limit of detection (LOD) of 1-10 µg/mL. The normal physiological range of SAA is about or less than 10 µg/mL in healthy adults. SSA is also an acute phase marker that responds rapidly. Similar to CRP, levels of acute-phase SAA increase within hours after inflammatory stimulus, and the magnitude of increase can be greater than that of CRP.

There is provided methods and device systems for detecting a rapid assay to detect acute phase reactants (ARPs) such as C-reactive protein (CRP) or serum amyloid A (SAA) in a body fluid sample in humans. The present device utilizes a capturing agent capable of capturing the acute phase reactants (e.g., CRP and/or SAA) and a detecting agent capable of detecting the presence of the acute phase reactants. The capturing agent includes a plurality of beads coupled with an antibody targeted against specific acute phase reactants and the detecting agent includes an anti-acute phase reactant antibody for detection. In one aspect, the present invention provides a method for measuring an analyte in a liquid sample, comprising: (a) obtaining a liquid sample contains or suspected of containing an analyte; (b) obtaining a sample holder configured to hold the liquid sample, said sample holder comprises: (i) a capturing agent conjugated to a microstructure that is immobilized in the sample holder, and (ii) a detecting agent that is immobilized in the sample holder; (c) depositing the liquid sample in the sample holder; (d) compressing the sample holder, wherein the deposited liquid sample comes into contact with the capturing agent and the detecting agent, wherein the capturing agent is configured to specifically bind to the analyte to form a complex, and wherein the detecting agent is configured to be diffusible in the liquid sample and bind to the complex to generate a signal, (e) incubating the compressed liquid sample; and (f) detecting the generated signal in the incubated liquid sample so as to measure the analyte. In certain embodiments, the analyte is a biomarker, indicative of the presence or severity of a disease or condition. In some embodiments, the analyte is an acute phase reactant. More In some embodiments, the analyte is C-reactive protein (CRP) or serum amyloid A (SAA). In some embodiments, the body fluid is whole blood, serum or plasma. More In some embodiments, the body fluid is whole blood. In certain embodiments, the sample holder can be a QMAX card that comprises wells or sample regions that are configured to hold the liquid sample. The sample holder comprises: (a) a first plate, (b) a second plate, and (c) a plurality of spacers, wherein the spacers are fixed onto either the first plate, the second plate, or both plates. The plates are moveable relative to each other into different configurations, including an open configuration and a closed configuration. In the open configuration: the two plates are separated apart, the spacing between the plates is not regulated by the spacers, and the liquid sample is deposited on one or both of the plates. In the closed configuration, which is configured after the liquid sample deposition in the open configuration: at least part of the liquid sample is compressed by the two plates into a layer of highly uniform thickness and is substantially stagnant relative to the plates, wherein the uniform thickness of the layer is regulated by the plates and the spacers. The plates are pressed against each other, compressing the liquid sample into a thin layer. In some embodiments, each of the plates has a thickness of 500 nm or less, 1,000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values. In some embodiments, at least one of the plates has a thickness of 100 mm or less, 50 mm or less, 25 mm or less, 10 mm or less, 5 mm or less, 1 mm or less, 500 μm or less, 400 μm or less, 300 μm or less, 200 μm or less, 175 μm or less, 150 μm or less, 125 μm or less, 100 μm or less, 75 μm or less, 50 μm or less, 40 μm or less, 30 μm or less, 20 μm or less, 10 μm or less, 5 μm or less, 4 μm or less, 3 μm or less, 2 μm or less, 1.8 μm or less, 1.5 μm or less, 1 μm or less, 0.5 μm or less, 0.2 μm or less, or 0.1 μm or less, including intermediate values and ranges. More In some embodiments, one of the plates has a thickness in the range of 0.5 mm to 1.5 mm; around 1 mm; in the range of 0.15 mm to 0.2 mm; or around 0.175 mm. In some embodiments, the first plate and second plate are configured to compress the sample into a layer of uniform thickness that substantially equals the height of the spacers. At least one of the plates has a lateral area of 1 mm² or less, 10 mm² or less, 25 mm² or less, 50 mm² or less, 75 mm² or less, 1 cm² (square centimeter) or less, 2 cm² or less, 3 cm² or less, 4 cm² or less, 5 cm² or less, 10 cm² or less, 100 cm² or less, 500 cm² or less, 1000 cm² or less, 5000 cm² or less, 10,000 cm² or less, 10,000 cm² or less, including intermediate values and ranges. In some embodiments, at least one of the plates has a lateral area of from 500 to 1000 mm²; or around 750 mm². In some embodiments, at least one of the plates is transparent, and is made from a flexible polymer. In some embodiments, the first and second plates are connected by a hinge that is a separate material (or a single piece of material) to the plates, and are configured to be changed from the open configuration to the closed configuration by folding the plates along the hinge. In some embodiments, one or both plates further comprises a scale marker, image marker, or location marker either on a surface of or inside the plate, that provide information of a lateral dimension of a structure of the sample and/or the plate. In some embodiments, the spacers are fixed on one or both of the plates and have a uniform height. In some embodiments, the spacers have a uniform height of 1 mm or less, 500 μm or less, 400 μm or less, 300 μm or less, 200 μm or less, 175 μm or less, 150 μm or less, 125 μm or less, 100 μm or less, 75 μm or less, 50 μm or less, 40 μm or less, 30 μm or less, 20 μm or less, 10 μm or less, 5 μm or less, 4 μm or less, 3 μm or less, 2 μm or less, 1.8 μm or less, 1.5 μm or less, 1 μm or less, 0.5 μm or less, 0.2 μm or less, 0.1 μm or less, 50 nm or less, 20 nm or less, 10 nm or less, including intermediate values and ranges. More In some embodiments, the spacers have a uniform height of from 0.5 to 2 μm, 0.5-3 μm, 0.5-5 μm, 0.5-10 μm, 0.5-20 μm, 0.5-30 μm, or 0.5-50 μm. In some embodiments, the spacers have a uniform height and a constant inter-spacer distance, and have a Young's modulus value and a filling factor value, so that the Young's modulus of the spacers times filling factor of the spacers equal to or larger than 10 MPa, wherein the filling factor is the ratio of the spacer area (one flat end) in contact with the layer of uniform thickness to the total plate area in contact with the layer of uniform thickness. More In some embodiments, the thickness of the plate times the Young's modulus of the flexible plate is in the range 60 to 750 GPa-μm. More In some embodiments, the fourth power of the inter-spacer-distance (ISD) divided by the thickness of the flexible plate (h) and the Young's modulus (E) of the flexible plate, $ISD^4/(hE)$, is equal to or less than $10^6$ μm³/GPa. In some embodiments, the inter-spacer distance is in the range of 7 μm to 50 μm, 50 μm to 120 μm or 120 μm to 200 μm. In some embodiments, the spacers are pillars with a cross-sectional shape selected from round, polygonal, circular, square, rectangular, oval, elliptical, or any super-positional combination. The spacers have a pillar shape and have a substantially flat top surface, wherein, for each spacer, the ratio of the lateral dimension of the spacer to its height is at least 1. Each spacer has the ratio of the lateral dimension of the spacer to its height is at least 1. In some embodiments, the minimum lateral dimension of spacer is less than or substantially equal to the minimum dimension of an analyte in the liquid sample—in the range of 0.5 μm to 100 μm, or 0.5 μm to 10 μm. In some embodiments, the spacers have a density of at least 100/mm², or 1,000/mm². In some embodiments, the spacers are fixed on a plate by directly embossing the plate or injection molding of the plate. More In some embodiments, the spacers are selected from polystyrene, PMMA, PC, COC, COP, or like plastics. In some embodiments, the liquid sample is compressed into a layer of uniform thickness that substantially equals uniform height of spacers that are fixed to one or both of the plates. The liquid sample is compressed into a layer of uniform thickness that has a variation of less than 15%, 10%, 5%, 2%, 1%, including intermediate values and ranges. In some embodiments, the liquid sample is compressed into a layer of uniform thickness of 500 nm or less, 1,000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values. More In some embodiments, the thin layer that has an average thickness of 500 μm, 400 μm, 300 μm, 200 μm, 175 μm, 150 μm, 125 μm, 100 μm, 75 μm, 50 μm, 40 μm, 30 μm, 20 μm, 10 μm, 5 μm, 4 μm, 3 μm, 2 μm, 1.8 μm, 1.5 μm, 1 μm, 0.5 μm, 0.2 μm, 0.1 μm, 50 nm, 20 nm, or 10 nm, including intermediate values and ranges. In some embodiments, at least part of the liquid sample is compressed into a thin layer that has an average thickness of in a range of 0.5-2 μm, 0.5-3 μm, 0.5-5 μm, 0.5-10 μm, 0.5-20 μm, 0.5-30 μm, or 0.5-50 μm, 25 μm or less, 10 μm or less, 5 μm or less, 3 μm or less, 2 μm or less, 1 μm or less, or 500 nm or less, 0.5-2 μm, 0.5-3 μm, or 0.5-5 μm. More In some embodiments, the average thickness of the layer of uniform thickness is in the range of 2 μm to 2.2 μm, 2.2 μm to 2.6 μm., or 1.8 μm to 2 μm and 0.6 μm to 3.8 μm, 1.8 μm to 3.8 μm and the sample is whole blood without a dilution by another liquid. More In some embodiments, the average thickness of the layer of uniform thickness is about equal to a minimum dimension of an analyte in the sample. In some embodiments, the microstructure is a plurality of beads or NHS activated beads, which have an average diameter of 100 nm, 200 nm, 500 nm, 1 μm, 2 μm, 5 μm, 10 μm, 20 μm, 50 μm, 100 μm, 200 μm, 500 μm, or 1 mm, including intermediate values and ranges. More In some embodiments, the average diameter of 1 μm to 10 μm, or 10 μm to 50 μm. In certain embodiments, the beads are made of polystyrene. The polystyrene can be obtained from Bangs Laboratories, Inc. (catalog no. PC08001). The size of the polystyrene beads is about 9.94 μm (diameter) with a packaging concentration (10.2% solids (100 mg/mL). The conjugation buffer containing the polystyrene beads is HEPES (pH 8.). The final working concentration of the polystyrene beads is 10 mg/mL. In some embodiments, the liquid sample further comprises an aggregation agent that induces aggregation of the interference elements. The aggregation agent induces aggregation of red blood cells, which comprises fibrinogen, thrombin, prothrombin, a dextran fraction selected from the group consisting of Dx-500, Dx-100, and Dx-70, poly(ethylene glycol), polyvinylprrolidone (PVP) selected from the group consisting of PVP-360 and PVP-40, or any combination thereof.

The aggregation agent is configured to induce the aggregation of at least 50%, 60%, 70%, 80%, 90%, or 95% of the red blood cells in the sample within 1, 2, 5, 10, 20, 30, or 60 minutes, including intermediate values and ranges. In some embodiments, the capturing agent is a first anti-CRP antibody. In some embodiments, the first anti-CRP antibody is a monoclonal antibody. In some embodiments, the detecting agent is a second anti-CRP antibody. In some embodiments, the second anti-CRP antibody is a monoclonal antibody. The second anti-CRP antibody can be labeled with a fluorophore. In some embodiments, the capture agent is a first anti-SAA antibody. In some embodiments, the first anti-SAA antibody is a monoclonal antibody. In some embodiments, the detecting agent is a second anti-SAA antibody. In some embodiments, the second anti-SAA antibody is a monoclonal antibody. The second anti-SAA antibody can be labeled with a fluorophore. In some embodiments, the deposited sample is not washed. In some embodiments, the incubating step is performed in about 30 seconds. In some embodiments, the incubating step is performed in about 60 seconds. In some embodiments, the incubating step is performed in about 90 seconds. In some embodiments, the detecting step is performed with an imager comprising a camera. The imager is a part or the entirety of the detector. In some embodiments, the imager is directed by the software to capture one or more images of the sample, identify the interference element regions and the interference element free regions, and digitally separate the interference element regions from the interference element free regions. In some embodiments, the filter is configured to filter signals from the sample. In some embodiments, the imager comprises a light source that is configured to illuminate the sample. In some embodiments, the detecting step is performed using a detector. In some embodiments, the detector is a mobile device, or a smart phone. In some embodiments, the detector comprises a display that is configured to show the presence and/or amount of the analyte. In some embodiments, the detector is configured to transmit detection results to a third party. In some embodiments, the detector comprises a software stored in a storage unit, and direct the detector to display the presence and/or amount of the analyte. The software is configured to direct the imager to calculate the combined signal of the analyte from the interference element free regions and disregard the signal of the analyte from the interference element regions as well as to increase signal contrast of the signals. In some embodiments, the present device is designed to measure analyte of interest useful in diagnostics, management, and/or prevention of human diseases and conditions, agricultural or veterinary applications, food testing or drug testing.

In some embodiments, the present assay is used for a colorimetric assay, a fluorescence assay. In some embodiments, the signal generated related to the analyte is an electrical signal or an optical signal.

In some embodiments, the signal related to the analyte is an optical signal that allows the imager to capture images of the interference element rich region and the interference element poor region. In some embodiments, the signal related to the analyte is from a colorimetric reaction, or produced by illuminating the sample with an illumination source. In another aspect, the present invention provides a method for measuring an analyte in a liquid sample, comprising: (a) obtaining a first plate and a second plate, wherein (i) each plate comprises, on its respective inner surface, a sample contact area that is configured to contact a liquid sample, (ii) a capturing agent is conjugated to microstructures that are immobilized on the sample contact area of one or both of the plates, (iii) the capturing agent is configured to specifically bind to the analyte, (iv) a detecting agent is immobilized on the sample contact area of one or both of the plates, and (v) the detecting agent is configured to be diffusible in the sample and bind to a complex of the capturing agent and the analyte; (b) depositing the sample in the sample contact area, wherein the sample comprises the analyte; (c) pressing the first plate and the second plate to compress the sample into a thin layer, which is at least partly confined by the two sample contact areas that face each other; (d) incubating for about 60 seconds or less; and (e) detecting the analyte by imaging the sample layer and detecting signals from the detecting agent that binds to the complex of the capturing agent and the analyte. In another aspect, the present invention provides a method for measuring acute phase reactants (such as C-reactive protein (CRP) or serum amyloid A (SAA) in a blood sample, comprising: (a) obtaining a first plate and a second plate, wherein each plate comprises, on its respective inner surface, a sample contact area that is configured to contact a blood sample, wherein an antibody to the acute phase reactant is conjugated to microstructures that are immobilized on the sample contact area of one or both of the plates, a fluorescent labeling antibody is immobilized on the sample contact area of one or both of the plates, and the detecting agent is configured to be diffusible in the sample and bind to a complex of the capturing agent and the acute phase reactant; (b) depositing the blood sample in the sample contact area, wherein the sample comprises the acute phase reactant; (c) pressing the first plate and the second plate to compress the sample into a thin layer, which is at least partly confined by the two sample contact areas that face each other; (d) incubating, after step (c), for about 60 seconds or less; and (e) detecting, after step (d), without a wash and without opening the plates, the analyte by imaging the sample layer and detecting signals from the detecting agent that binds to the complex of the acute phase reactant and acute phase reactant antibody. In another aspect, the present invention provides a method for measuring C-reactive protein (CRP) in a blood sample, comprising: (a) obtaining a first plate and a second plate, wherein each plate comprises, on its respective inner surface, a sample contact area that is configured to contact a liquid sample, wherein an antibody to CRP is conjugated to microstructures that are immobilized on the sample contact area of one or both of the plates, a labeling antibody is immobilized on the sample contact area of one or both of the plates, the detecting agent is configured to be diffusible in the sample and bind to a complex of the capturing agent and the CRP, the plates are moveable relative to each other in different configurations, including an open configuration and a closed configuration, wherein in the open configuration, the plates are partly or entirely separated apart with an average gap of more than 300 µm between the plates, and in the closed configuration, the plates are pressed against each other with a gap of less than 200 µm between the plates; (b) depositing the sample in the sample contact area when the plates are in the open configuration, wherein the blood sample comprises CRP; (c) changing the plates into a closed configuration, compressing the sample into a thin layer, which is at least partly confined by the two sample contact areas that face each other; (d) incubating, after step (c), for about 60 seconds or less; and (e) detecting, after step (d), without a wash and without opening the plates, the analyte by imaging the sample layer and detecting signals from the detecting agent that binds to the complex of the CRP and CRP antibody. In another aspect, the present invention provides a method for measuring serum amyloid A (SAA) in a blood sample, comprising: (a) obtaining a first plate and a second plate, wherein each plate comprises, on its respective inner surface, a sample contact area that is configured to contact a liquid sample, wherein an antibody to SAA is conjugated to microstructures that are immobilized on the sample contact area of one or both of the plates, a labeling antibody is immobilized on the sample contact area of one or both of the plates, the detecting agent is configured to be diffusible in the sample and bind to a complex of the capturing agent and the SAA, the plates are moveable relative to each other in different configurations, including an open configuration and a closed configuration, wherein in the open configuration, the plates are partly or entirely separated apart with an average gap of more than 300 µm between the plates, and in the closed configuration, the plates are pressed against each other with a gap of less than 200 µm between the plates; (b) depositing the sample in the sample contact area when the plates are in the open configuration, wherein the blood sample comprises SAA; (c) changing the plates into a closed configuration, compressing the sample into a thin layer, which is at least partly confined by the two sample contact areas that face each other; (d) incubating, after step (c), for about 60 seconds or less; and (e) detecting, after step (d), without a wash and without opening the plates, the analyte by imaging the sample layer and detecting signals from the detecting agent that binds to the complex of the CRP and CRP antibody. In yet another aspect, the present invention provides an apparatus for measuring an analyte in a liquid sample, comprising: (a) a sample holder that is configured to hold a liquid sample that contains the analyte, wherein: (i). a capturing agent conjugated to microstructures that are immobilized in the sample holder, (ii) a detecting agent immobilized in the sample holder, (iii) the capturing agent is configured to specifically bind to the analyte, and (iv) the detecting agent is configured to be diffusible in the sample and bind to a complex of the capturing agent and the analyte; the detecting agent is configured to be diffusible in the sample and bind to a complex of the capturing agent and the analyte; and (b) an adaptor that is configured to accommodate the sample holder and be attachable to a mobile device, wherein: (i) the mobile device comprises an imager, (ii) the adaptor is configured to position the sample in a field of view (FOV) of the imager when the adaptor is attached to the mobile device, and (iii) the imager is configured to capture images of the sample, thereby detecting/measuring a signal that is generated by the binding of the biomarker with the capturing agent after the sample is incubated with the capturing agent for about 60 seconds or less.

Exemplary Embodiments

In one aspect, the present invention provides a method for measuring an analyte in a liquid sample, comprising: (a) obtaining a sample holder that is configured to hold a liquid sample that contains an analyte, wherein: (i) a capturing agent is conjugated to micro/nanostructures that are immobilized in the sample holder, (ii) a detecting agent is immobilized in the sample holder, (iii) the capturing agent is configured to specifically bind to the analyte, and (iv) the detecting agent is configured to be diffusible in the sample and bind to a complex of the capturing agent and the analyte; (b) depositing the sample in the sample holder, wherein the sample is in contact with the capturing agent and the detecting agent in the sample holder; (c) adjusting the sample holder to compress the sample into a thin layer; (d) incubating for a predetermined period of time; and (e) detecting the analyte by imaging the sample layer and detecting signals from the detecting agent that binds to the complex of the capturing agent and the analyte.

In another aspect, the present invention provides a method for measuring an analyte in a liquid sample, comprising: (a) obtaining a first plate and a second plate, wherein each plate comprises: (i) on its respective inner surface, a sample contact area that is configured to contact a liquid sample, wherein capturing agent is conjugated to micro/nanostructures that are immobilized on the sample contact area of one or both of the plates, (ii) a detecting agent is immobilized on the sample contact area of one or both of the plates, (iii) the capturing agent is configured to specifically bind to the analyte, and (iv) the detecting agent is configured to be diffusible in the sample and bind to a complex of the capturing agent and the analyte; (b) depositing the sample in the sample contact area, wherein the sample comprises the analyte; (c) pressing the first plate and the second plate to compress the sample into a thin layer, which is at least partly confined by the two sample contact areas that face each other; (d) incubating for a predetermined period of time that is about 60 seconds or less; and (e) detecting the analyte by imaging the sample layer and detecting signals from the detecting agent that binds to the complex of the capturing agent and the analyte. In another aspect, the present invention provides a method for measuring C-reactive protein (CRP) in a liquid sample, comprising: (a) obtaining a first plate and a second plate, wherein each plate comprises: (i) on its respective inner surface, a sample contact area that is configured to contact a liquid sample, wherein an antibody to CRP is conjugated to micro/nanostructures that are immobilized on the sample contact area of one or both of the plates, (ii) a labeling antibody is immobilized on the sample contact area of one or both of the plates, and (iii) the detecting agent is configured to be diffusible in the sample and bind to a complex of the capturing agent and the CRP; (b) depositing the sample in the sample contact area, wherein the sample comprises CRP; (c) pressing the first plate and the second plate to compress the sample into a thin layer, which is at least partly confined by the two sample contact areas that face each other; (d) incubating, after step (c), for a predetermined period of time that is about 60 seconds or less; and (e) detecting, after step (d), without a wash and without opening the plates, the analyte by imaging the sample layer and detecting signals from the detecting agent that binds to the complex of the CRP and CRP antibody. In another aspect, the present invention provides a method for measuring C-reactive protein (CRP) in a liquid sample, comprising: (a) obtaining a first plate and a second plate, wherein each plate comprises: (i) on its respective inner surface, a sample contact area that is configured to contact a liquid sample, wherein an antibody to CRP is conjugated to micro/nanostructures that are immobilized on the sample contact area of one or both of the plates, (ii) a labeling antibody is immobilized on the sample contact area of one or both of the plates, (iii) the detecting agent is configured to be diffusible in the sample and bind to a complex of the capturing agent and the CRP, (iv) the plates are moveable relative to each other in different configurations, including an open configuration and a closed configuration, wherein in the open configuration, the plates are partly or entirely separated apart with an average gap of more than 300 µm between the plates, and in the closed configuration, the plates are pressed against each other with a gap of less than 200 µm between the plates; (b) depositing the sample in the sample contact area when the plates are in the open configuration, wherein the sample comprises CRP; (c) changing the plates into a closed configuration, compressing the sample into a thin layer, which is at least partly confined by the two sample contact areas that face each other; (d) incubating, after step (c), for a predetermined period of time that is about 60 seconds or less; and (e) detecting, after step (d), without a wash and without opening the plates, the analyte by imaging the sample layer and detecting signals from the detecting agent that binds to the complex of the CRP and CRP antibody. In another aspect, the present invention provides an apparatus for measuring an analyte in a liquid sample, comprising: (a) a sample holder that is configured to hold a liquid sample that contains the analyte, wherein (i) a capturing agent is conjugated to micro/nanostructures that are immobilized in the sample holder, (ii) a detecting agent is immobilized in the sample holder, (iii) the capturing agent is configured to specifically bind to the analyte, and (iv) the detecting agent is configured to be diffusible in the sample and bind to a complex of the capturing agent and the analyte; the detecting agent is configured to be diffusible in the sample and bind to a complex of the capturing agent and the analyte; and (b) an adaptor that is configured to accommodate the sample holder and be attachable to a mobile device, wherein (i) the mobile device comprises an imager, (ii) the adaptor is configured to position the sample in a field of view (FOV) of the imager when the adaptor is attached to the mobile device, and (iii) the imager is configured to capture images of the sample, thereby detecting/measuring a signal that is generated by the binding of the biomarker with the capturing agent after the sample is incubated with the capturing agent for a predetermined period of time that is about 60 seconds or less. In certain embodiments, micro/nanostructures are beads. The micro/nanostructures can be NHS activated beads. In certain embodiments, the beads can have an average diameter of 100 nm, 200 nm, 500 nm, 1 µm, 2 µm, 5 µm, 10 µm, 20 µm, 50 µm, 100 µm, 200 µm, 500 µm, or 1 mm, including intermediate values and ranges. In some embodiments, the beads can have an average diameter in the range of 1 µm to 10 µm, or 10 µm to 50 µm.

During the incubating step (d), the predetermined period of time can be about 90 seconds or less, about 60 seconds or less, or about 30 seconds or less. In certain embodiments, the sample contact area(s) of one or both of the plates are not washed after step (d). In certain embodiments, the capturing agent is an antibody. Polyclonal antibody or monoclonal antibody can be used. In certain preferred embodiments, the capture agent is a monoclonal antibody (specifically binds CRP). In certain embodiments, the detecting agent is labeled with a fluorophore. In certain embodiments, the analyte is C-reactive protein (CRP). In certain embodiments, at least part of the sample is compressed into a thin layer that has an average sample thickness of 500 µm, 400 µm, 300 µm, 200 µm, 175 µm, 150 µm, 125 µm, 100 µm, 75 µm, 50 µm, 40 µm, 30 µm, 20 µm, 10 µm, 5 µm, 4 µm, 3 µm, 2 µm, 1.8 µm, 1.5 µm, 1 µm, 0.5 µm, 0.2 µm, 0.1 µm, 50 nm, 20 nm, or 10 nm, including intermediate values and ranges. In certain preferred embodiments, the average sample thickness is in a range of 0.5-2 µm, 0.5-3 µm, 0.5-5 µm, 0.5-10 µm, 0.5-20 µm, 0.5-30 µm, or 0.5-50 µm. In certain more preferred embodiments, the average sample thickness in the range of 0.5-2 µm, 0.5-3 µm, or 0.5-5 µm. In yet certain preferred embodiments, the average sample thickness is 25 µm or less, 10 µm or less, 5 µm or less, 3 µm or less, 2 µm or less, 1 µm or less, or 500 nm or less. In certain embodiments, the sample is a bodily fluid. In certain embodiments, bodily fluid is blood, saliva or urine. In certain embodiments, when the sample is whole blood without a dilution by another liquid, or processed forms of blood. In certain embodiments, the sample can comprise an aggregation agent that induces aggregation of the interference elements. In certain embodiments, the sample is original, diluted, or processed forms of: bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate. When the sample is blood, the average thickness of the layer of uniform thickness is in the range of 1.8 µm to 3.8 µm. In certain embodiments, the average thickness of the layer of uniform thickness is about equal to a minimum dimension of an analyte in the sample. In certain embodiments, the average thickness of the layer of uniform thickness is in the range of 2 µm to 2.2 µm. In certain embodiments, the average thickness of the layer of uniform thickness is in the range of 2.2 µm to 2.6 µm. In certain embodiments, the average thickness of the layer of uniform thickness is in the range of 1.8 µm to 2 µm. In certain embodiments, the average thickness of the layer of uniform thickness is in the range of 2.6 µm to 3.8 µm. In certain embodiments, the analyte is a biomarker, an environmental marker, or a foodstuff marker. In certain embodiments, the analyte is a biomarker indicative of the presence or severity of a disease or condition. In certain embodiments, the analyte is a cell, a protein, or a nucleic acid. In certain preferred embodiments, the analyte is C-reactive protein (CRP). In the present invention, the sample holder comprises wells that configured to hold the sample. The sample holder comprises a first plate, and a second plate, and spacers. The spacers are configured to regulate a gap between the plates when the plates are pressed against each, compressing the sample into a thin layer. In certain embodiments, the sample holder comprises a first plate, a second plate, and spacers, and wherein: (i) the plates are moveable relative to each other into different configurations, including an open configuration and a closed configuration; (ii) in the open configuration: the two plates are separated apart, the spacing between the plates is not regulated by the spacers, and the sample is deposited on one or both of the plates; and (iii) in the closed configuration, which is configured after the sample deposition in the open configuration: at least part of the sample is compressed by the two plates into a layer of highly uniform thickness and is substantially stagnant relative to the plates, wherein the uniform thickness of the layer is regulated by the plates and the spacers. In certain embodiments, the sample holder comprises a Q-card, which comprises a first plate, a second plate, and spacers, wherein the spacers are configured to regulate a gap between the plates when the plates are pressed against each, compressing the sample into a thin layer. In certain embodiments, the spacers have a uniform height and a constant inter-spacer distance; and the sample is compressed by the sample holder into a thin layer with a uniform thickness that is regulated by the height of the spacers. In certain embodiments, the sample is compressed into a layer of uniform thickness that substantially equals uniform height of spacers that are fixed to one or both of the plates. In certain embodiments, the sample is compressed into a layer of uniform thickness that has a variation of less than 15%, 10%, 5%, 2%, 1%, including intermediate values and ranges. In certain embodiments, the sample, when compressed, has a thickness of 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, including intermediate values and ranges.

In certain embodiments, the sample holder comprises a first plate and a second plate, wherein each of the plate has a thickness of 500 nm or less, 1,000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, including intermediate values and ranges. In certain embodiments, the aggregation agent is used to induce aggregation of the interference elements. In certain embodiments, the sample comprises blood and an aggregation agent that induces aggregation of red blood cells. In certain embodiments, the aggregation agent includes, but not limited to, fibrinogen (and subunits thereof), thrombin and prothrombin, certain dextran fractions (e.g., Dx-500, Dx-100, and Dx-70), poly(ethylene glycol), or polyvinylprrolidone (PVP, e.g. PVP-360 and PVP-40), or any combination thereof. In certain embodiments, the aggregation agent is configured to induce the aggregation of at least 50%, 60%, 70%, 80%, 90%, or 95% of the red blood cells in the sample within 1, 2, 5, 10, 20, 30, or 60 minutes, including intermediate values and ranges. In certain embodiments, the imager comprises a camera. In certain embodiments, the imager is a part of the detector or the entirety of the detector. In certain embodiments, the imager is directed by the software to capture one or more images of the sample, identify the interference element regions and the interference element free regions, and digitally separate the interference element regions from the interference element free regions. In certain embodiments, the imager comprises a filter that is configured to filter signals from the sample. In certain embodiments, the imager comprises a light source that is configured to illuminate the sample. In certain embodiments, the detector is a mobile device. In certain embodiments, the detector is a smart phone. In certain embodiments, the detector is a smart phone and the imager is a camera as part of the smart phone. In certain embodiments, the detector comprises a display that is configured to show the presence and/or amount of the analyte. In certain embodiments, the detector is configured to transmit detection results to a third party. In certain embodiments, the software is stored in a storage unit, which is part of the detector. In certain embodiments, the software is configured to direct the detector to display the presence and/or amount of the analyte. In certain embodiments, the software is configured to direct the imager to calculate the combined signal of the analyte from the interference element free regions. In certain embodiments, the software is configured to direct the imager to disregard the signal of the analyte from the interference element regions. In certain embodiments, the software is configured to direct the imager to increase signal contrast of the signals from the interference element regions to the signals from the interference element free regions. In certain embodiments, the software is configured to direct the detector to calculate a ratio of the signal from the interference element regions to the interference element free regions. In certain embodiments, the apparatus or method of the present in invention are used for detection of proteins, peptides, nucleic acids, synthetic compounds, inorganic compounds, organic compounds, bacteria, virus, cells, tissues, nanoparticles, and other molecules, compounds, mixtures and substances thereof. In certain embodiments, the apparatus or method of the present invention can be used for diagnostics, management, and/or prevention of human diseases and conditions. In certain embodiments, the apparatus or method of the present invention can be used for prevention or treatment of veterinary diseases and conditions. In certain embodiments, the apparatus or method of the present invention can be used for diagnostics, management, and/or prevention of plant diseases and conditions. In certain embodiments, the present apparatus or method can be used for environments testing and decontamination. In certain embodiments, the present apparatus or method can be used for agricultural or veterinary applications. In certain embodiments, the present apparatus or method can be used for food testing. In certain embodiments, the present apparatus or method can be used for drug testing and abuse prevention. In certain embodiments, the present apparatus or method can be used for detecting and/or measuring an analyte in blood. In certain embodiments, the present apparatus or method can be used for a colorimetric assay. In certain embodiments, the present apparatus or method can be used for a fluorescence assay. In certain embodiments, the signal related to the analyte is an electrical signal or an optical signal. In certain embodiments, the signal related to the analyte is an optical signal that allows the imager to capture images of the interference element rich region and the interference element poor region. In certain embodiments, the signal related to the analyte is from a colorimetric reaction. In certain embodiments, the signal related to the analyte is produced by illuminating the sample with an illumination source. In certain embodiments, the plates are movable relative to each. In certain embodiments, the spacers are fixed on one or both of the plates and have a uniform height. In certain embodiments, the first plate and second plate are configured to compress the sample into a layer of uniform thickness that substantially equals the height of the spacers. In certain embodiments, the spacers have a uniform height of 1 mm or less, 500 μm or less, 400 μm or less, 300 μm or less, 200 μm or less, 175 μm or less, 150 μm or less, 125 μm or less, 100 μm or less, 75 μm or less, 50 μm or less, 40 μm or less, 30 μm or less, 20 μm or less, 10 μm or less, 5 μm or less, 4 μm or less, 3 μm or less, 2 μm or less, 1.8 μm or less, 1.5 μm or less, 1 μm or less, 0.5 μm or less, 0.2 μm or less, 0.1 μm or less, 50 nm or less, 20 nm or less, 10 nm or less, including intermediate values and ranges. In certain embodiments, the spacers are pillars with a cross-sectional shape selected from round, polygonal, circular, square, rectangular, oval, elliptical, or any super-positional combinations thereof. In certain embodiments, the spacers have pillar shape and have a substantially flat top surface, wherein, for each spacer, the ratio of the lateral dimension of the spacer to its height is at least 1. In certain embodiments, the spacers have a pillar shape, and the sidewall corners of the spacers have a round shape with a radius of curvature at least 1 µm. In certain embodiments, the spacers have a density of at least 1,000/ mm². In certain embodiments, at least one of the plates is transparent. In certain embodiments, at least one of the plates is made from a flexible polymer. In certain embodiments, only one of the plates is flexible. In certain embodiments, the spacers have a uniform height in the range of 0.5-2 µm, 0.5-3 µm, 0.5-5 µm, 0.5-10 µm, 0.5-20 µm, 0.5-30 µm, or 0.5-50 µm. In certain embodiments, the inter-spacer distance is in the range of 14 µm to 200 µm. In certain embodiments, the inter-spacer distance is in the range of 7 µm to 20 µm. In certain embodiments, at least one of the plates has a thickness of 100 mm or less, 50 mm or less, 25 mm or less, 10 mm or less, 5 mm or less, 1 mm or less, 500 µm or less, 400 µm or less, 300 µm or less, 200 µm or less, 175 µm or less, 150 µm or less, 125 µm or less, 100 µm or less, 75 µm or less, 50 µm or less, 40 µm or less, 30 µm or less, 20 µm or less, 10 µm or less, 5 µm or less, 4 µm or less, 3 µm or less, 2 µm or less, 1.8 µm or less, 1.5 µm or less, 1 µm or less, 0.5 µm or less, 0.2 µm or less, or 0.1 µm or less, including intermediate values and ranges. In certain preferred embodiments, at least one of the plates has a thickness in the range of 0.5 to 1.5 mm; around 1 mm; in the range of 0.15 to 0.2 mm; or around 0.175 mm. In certain embodiments, at least one of the plates has a lateral area of 1 mm² or less, 10 mm² or less, 25 mm² or less, 50 mm² or less, 75 mm² or less, 1 cm² (square centimeter) or less, 2 cm² or less, 3 cm² or less, 4 cm² or less, 5 cm² or less, 10 cm² or less, 100 cm² or less, 500 cm² or less, 1000 cm² or less, 5000 cm² or less, 10,000 cm² or less, 10,000 cm² or less, including intermediate values and ranges. In certain preferred embodiments, at least one of the plates has a lateral area of in the range of 500 to 1000 mm²; or around 750 mm². In certain embodiments, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness. In certain embodiments, the thickness of the flexible plate times the Young's modulus of the flexible plate is in the range 60 to 750 GPa-µm. In certain embodiments, for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ µm³/GPa. In certain embodiments, one or both plates comprise a location marker, either on a surface of or inside the plate, that provide information of a location of the plate. In certain embodiments, one or both plates comprise a scale marker, either on a surface of or inside the plate, that provide information of a lateral dimension of a structure of the sample and/or the plate. In certain embodiments, one or both plates comprise an image marker, either on a surface of or inside the plate, that assists an imaging of the sample. In certain embodiments, the inter-spacer distance is in the range of 7 µm to 50 µm. In certain preferred embodiments, the inter-spacer distance is in the range of 50 µm to 120 µm. In certain preferred embodiments, the inter-spacer distance is in the range of 120 µm to 200 µm. In certain embodiments, the spacers are pillars with a cross-sectional shape selected from round, polygonal, circular, square, rectangular, oval, elliptical, or any super-positional combination thereof. In certain preferred embodiments, the spacers have a pillar shape and have a substantially flat top surface, wherein, for each spacer, the ratio of the lateral dimension of the spacer to its height is at least 1. In certain preferred embodiments, each spacer has the ratio of the lateral dimension of the spacer to its height is at least 1. In certain embodiments, the minimum lateral dimension of spacer is less than or substantially equal to the minimum dimension of an analyte in the sample. In certain embodiments, the minimum lateral dimension of spacer is in the range of 0.5 µm to 100 µm.

In certain embodiments, the minimum lateral dimension of spacer is in the range of 0.5 µm to 10 µm. In certain embodiments, the spacers have a pillar shape, and the sidewall corners of the spacers have a round shape with a radius of curvature at least 1 □m. In certain embodiments, the spacers have a density of at least 100/mm². In certain embodiments, the spacers have a density of at least 1,000/ mm². In certain embodiments, at least one of the plates is transparent. In certain embodiments, at least one of the plates is made from a flexible polymer. In certain embodiments, for a pressure that compresses the plates, the spacers are not compressible and/or, independently, only one of the plates is flexible. In certain embodiments, the flexible plate has a thickness in the range of 10 µm to 200 µm. In certain embodiments, the variation of sample thickness is less than 30%. In certain preferred embodiments, the variation of sample thickness is less than 10%. In certain preferred embodiments, the variation of sample thickness is less than 5%. In certain embodiments, the first and second plates are connected and are configured to be changed from the open configuration to the closed configuration by folding the plates. In certain embodiments, the first and second plates are connected by a hinge and are configured to be changed from the open configuration to the closed configuration by folding the plates along the hinge. In certain embodiments, the first and second plates are connected by a hinge that is a separate material to the plates, and are configured to be changed from the open configuration to the closed configuration by folding the plates along the hinge. In certain embodiments, the first and second plates are made in a single piece of material and are configured to be changed from the open configuration to the closed configuration by folding the plates. In certain embodiments, the layer of uniform thickness sample is uniform over a lateral area that is at least 1 mm². In certain embodiments, the average thickness of the layer of uniform thickness is about equal to a minimum dimension of an analyte in the sample. In certain embodiments, the spacers are fixed on a plate by directly embossing the plate or injection molding of the plate. In certain embodiments, the materials of the plate and the spacers are selected from polystyrene, PMMA, PC, COC, COP, or another plastic. In the present invention, the samples to be manipulated and/or analyzed can have a various range of viscosities. For examples, the typical viscosity range is 1.31 to 0.28 (mPa s) from 10 to 100° C. for water; 1.05 to 0.70 (mPa s) from 19 to 37° C. for PBS buffer; 2.4 to 1.45 (mPa s) from 17 to 45° C. for plasma; 2.87 to 2.35 (mPa s) from 35 to 42° C. for whole blood; and 0.797 to 0.227 (mPa s) from 0 to 100° C. for methanol. In certain embodiments, the sample has a viscosity from 0.1 to 4 (mPa s). In some embodiments, the sample has viscosity of from 4 to 50 (mPa s). In a preferred embodiment, the sample has viscosity of from 0.5 to 3.5 (mPa s). In certain embodiments of the present invention, the spacers are pillars that have a flat top and a foot fixed on one plate, wherein the flat top has a smoothness with a small surface variation, and the variation is less than 5, 10 nm, 20 nm, 30 nm, 50 nm, 100 nm, 200 nm, 300 nm, 400 nm, 500 nm, 600 nm, 700 nm, 800 nm, 1000 nm, including intermediate values and ranges. A preferred flat pillar top smoothness is that surface variation of 50 nm or less. Furthermore, the surface variation is relative to the spacer height and the ratio of the pillar flat top surface variation to the spacer height is less than 0.5%, 1%, 3%, 5%, 7%, 10%, 15%, 20%, 30%, 40%, including intermediate values and ranges. A preferred flat pillar top smoothness has a ratio of the pillar flat top surface variation to the spacer height is less than 2%, 5%, or 10%. In certain embodiments of the present invention, the spacers are pillars that have a sidewall angle. In some embodiments, the sidewall angle is less than 5 degrees (measured from the normal of a surface), 10, 20, 30, 40, 50, 70 degrees, including intermediate values and ranges. In a preferred embodiment, the sidewall angle is less 5, 10, or 20 degrees. In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that: (a) has a magnitude that is not precisely known or precisely predictable at the time the force is applied; (b) has a pressure in the range of 0.01 kg/cm$^2$ (centimeter square) to 100 kg/cm$^2$; (c) varies in magnitude from one application of the force to the next; and (d) the imprecision (i.e., the variation) of the force in (a) and (c) is at least 20% of the total force that actually is applied. An imprecise force can be applied by human hand, for example, e.g., by pinching an object together between a thumb and index finger, or by pinching and rubbing an object together between a thumb and index finger. In some embodiments, the imprecise force by the hand pressing has a pressure of 0.01 kg/cm$^2$, 0.1 kg/cm$^2$, 0.5 kg/cm$^2$, 1 kg/cm$^2$, 2 kg/cm$^2$, kg/cm$^2$, 5 kg/cm$^2$, 10 kg/cm$^2$, 20 kg/cm$^2$, 30 kg/cm$^2$, 40 kg/cm$^2$, 50 kg/cm$^2$, 60 kg/cm$^2$, 100 kg/cm$^2$, 150 kg/cm$^2$, 200 kg/cm$^2$, including intermediate values and ranges; and a preferred range of 0.1 kg/cm$^2$ to 0.5 kg/cm$^2$, 0.5 kg/cm$^2$ to 1 kg/cm$^2$, 1 kg/cm$^2$ to 5 kg/cm$^2$, 5 kg/cm$^2$ to 10 kg/cm$^2$ (pressure). The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling factor is the filling factor of the smallest spacer contact surface. For example, if the spacers are pillars with a flat top of a square shape (10 μm×10 μm), a nearly uniform cross-section and 2 μm tall, and the spacers are periodic with a period of 100 μm, then the filing factor of the spacer is 1%. If in the above example, the foot of the pillar spacer is a square shape of 15 μm×15 μm, then the filling factor is still 1% by the definition. In certain embodiments, the present method further comprises an analyzing step (e) that analyze the sample. The analyzing step (e) comprises calculating the volume of a relevant sample volume by measuring the lateral area of the relevant sample volume and calculating the volume from the lateral area and the predetermined spacer height. In certain embodiments, the analyzing step (e) comprises measuring: (i) imaging, (ii) luminescence selected from photoluminescence, electroluminescence, and electrochemiluminescence, (iii) surface Raman scattering, (iv) electrical impedance selected from resistance, capacitance, and inductance, or (v) any combination of (i)-(iv). In certain embodiments, the analyzing step (e) comprises reading, image analysis, or counting of the analyte, or a combination of thereof. In certain embodiments, the sample contains one or plurality of analytes, and one or both plate sample contact surfaces comprise one or a plurality of binding sites that each bind and immobilize a respective analyte. In certain embodiments, one or both plate sample contact surfaces comprise one or a plurality of storage sites that each stores a reagent or reagents, wherein the reagent(s) dissolve and diffuse in the sample during or after step (c). In certain embodiments, one or both plate sample contact surfaces comprise one or a plurality of amplification sites that are each capable of amplifying a signal from the analyte or a label of the analyte when the analyte or label is within 500 nm from an amplification site. In certain embodiments, the present method comprises: (i) one or both plate sample contact surfaces comprise one or a plurality of binding sites that each binds and immobilize a respective analyte; or (ii) one or both plate sample contact surfaces comprise, one or a plurality of storage sites that each stores a reagent or reagents; wherein the reagent(s) dissolve and diffuse in the sample during or after step (c), and wherein the sample contains one or plurality of analytes; or (iii) one or a plurality of amplification sites that are each capable of amplifying a signal from the analyte or a label of the analyte when the analyte or label is 500 nm from the amplification site; or (iv) any combination of (i) to (iii). In certain embodiments, the layer of uniform thickness in the closed configuration is less than 150 μm. In certain embodiments, the pressing is provided by a pressured liquid, a pressed gas, or a conformal material. In certain embodiments, the analyzing comprises counting cells in the layer of uniform thickness. In certain embodiments, the analyzing comprises performing an assay in the layer of uniform thickness. In certain embodiments, the sample deposited has a total volume less 0.5 μL. In certain embodiments, multiple drops of sample are deposited onto one or both of the plates. In certain embodiments, the inter-spacer distance is in the range of 1 μm to 120 μm. In certain embodiments, the inter-spacer distance is in the range of 120 μm to 50 μm. In certain embodiments, the inter-spacer distance is in the range of 120 μm to 200 μm. In certain embodiments, the flexible plates have a thickness in the range of 20 μm to 250 μm and Young's modulus in the range 0.1 to 5 GPa. In certain embodiments, the thickness of the flexible plate times the Young's modulus of the flexible plate is in the range 60 to 750 GPa-μm. In certain embodiments, the layer of uniform thickness sample is uniform over a lateral area that is at least 1 mm$^2$. In certain embodiments, the layer of uniform thickness sample is uniform over a lateral area that is at least 3 mm$^2$. In certain embodiments, the layer of uniform thickness sample is uniform over a lateral area that is at least 5 mm$^2$. In certain embodiments, the layer of uniform thickness sample is uniform over a lateral area that is at least 10 mm$^2$. In certain embodiments, the layer of uniform thickness sample is uniform over a lateral area that is at least 20 mm$^2$. In certain embodiments, the layer of uniform thickness sample is uniform over a lateral area that is in a range of 20 mm$^2$ to 100 mm$^2$. In certain embodiments, the layer of uniform thickness sample has a thickness uniformity of up to +1-5%, +/−10%, +/−20%, +/−30%, +/−40%, +/−50% or better. In certain embodiments, the spacers are pillars with a cross-sectional shape selected from round, polygonal, circular, square, rectangular, oval, elliptical, or any superpositional combination thereof. In certain embodiments, the spacers have pillar shape, have a substantially flat top surface, and have substantially uniform cross-section, wherein, for each spacer, the ratio of the lateral dimension of the spacer to its height is at least 1. In certain embodiments, the inter spacer distance is periodic. In certain embodiments, the spacers have a filling factor of 1% or higher, wherein the filling factor is the ratio of the spacer contact area to the total plate area. In certain embodiments, the Young's modulus of the spacers times the filling factor of the spacers is equal or larger than 20 MPa, wherein the filling factor is the ratio of the spacer contact area to the total plate area. In certain embodiments, the spacing between the two plates at the closed configuration is less than 200 µm. In certain embodiments, the spacing between the two plates at the closed configuration is a value selected from between 1.8 µm and 3.5 µm. In certain embodiments, the spacers are fixed on a plate by directly embossing the plate or injection molding of the plate. In certain embodiments, the materials of the plate and the spacers are selected from polystyrene, PMMA, PC, COC, COP, or like plastic. In certain embodiments, the spacers have a pillar shape, and the sidewall corners of the spacers have a round shape with a radius of curvature at least 1 µm. In certain embodiments, the spacers have a density of at least 1,000/mm$^2$. In certain embodiments, at least one of the plates is transparent. In certain embodiments, the mold used to make the spacers is fabricated by a mold containing features that are fabricated by either (a) directly reactive ion etching or ion beam etched, or (b) by a duplication or multiple duplication of the features that are reactive ion etched or ion beam etched. In certain embodiments, the spacers are configured, such that the filling factor is in the range of 1%-5%, 5%-10%, 10%-20%, or 20%-30%. In certain preferred embodiments, the spacers are configured, such that the filling factor is in the range of 1%-5%. In certain embodiments, the surface variation is relative to the spacer height and the ratio of the pillar flat top surface variation to the spacer height is less than 0.5%, 1%, 3%, 5%, 7%, 10%, 15%, 20%, 30%, 40%, including intermediate values and ranges. A preferred flat pillar top smoothness has a ratio of the pillar flat top surface variation to the spacer height is less than 2%, 5%, or 10%. In certain embodiments, the spacers are configured, such that the filling factor is 5%, 10%, 20%, 30%, 40%, 50%, or in a range of any two of the values. In certain embodiments, the filling factor is 50%, 60%, 70%, 80%, including intermediate values and ranges. In certain embodiments, the spacers are configured, such that the filling factor multiplies the Young's modulus of the spacer is in the range of 2 MPa and 10 MPa, 10 MPa and 20 MPa,. 20 MPa and 40 MPa, 40 MPa and 80 MPa, 80 MPa and 120 MPa, or 120 MPa to 150 MPa. In certain embodiments, the present device further comprises a dry reagent coated on one or both plates. In certain embodiments, the device further comprises, on one or both plates, a dry binding site that has a predetermined area, wherein the dry binding site binds to and immobilizes an analyte in the sample. In certain embodiments, the device further comprises, on one or both plates, a releasable dry reagent and a release time control material that delays the time that the releasable dry regent is released into the sample. In certain embodiments, the release time control material delays the time that the dry regent starts to be released into the sample by at least 3 seconds. In certain embodiments, the regent comprises anticoagulant and/or staining reagent(s). In certain embodiments, the reagent comprises cell lysing reagent(s). In certain embodiments, the device further comprises, on one or both plates, one or a plurality of dry binding sites and/or one or a plurality of reagent sites. In certain embodiments, the analyte comprises a molecule (e.g., a protein, peptides, DNA, RNA, nucleic acid, or other molecule), cells, tissues, viruses, and nanoparticles with different shapes. In certain embodiments, the analyte comprises white blood cells, red blood cells and platelets. In certain embodiments, the analyte is stained. In certain embodiments, the spacers regulating the layer of uniform thickness have a filling factor of at least 1%, wherein the filling factor is the ratio of the spacer area in contact with the layer of uniform thickness to the total plate area in contact with the layer of uniform thickness. In certain embodiments, for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness. In certain embodiments, wherein for a flexible plate, the thickness of the flexible plate times the Young's modulus of the flexible plate is in the range 60 to 750 GPa-m. In certain embodiments, for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ µm$^3$/GPa. In certain embodiments, one or both plates comprise a location marker, either on a surface of or inside the plate, that provide information of a location of the plate. In certain embodiments, one or both plates comprise a scale marker, either on a surface of or inside the plate, that provide information of a lateral dimension of a structure of the sample and/or the plate. In certain embodiments, one or both plates comprise an imaging marker, either on surface of or inside the plate, that assists an imaging of the sample. In certain embodiments, the spacers functions as a location marker, a scale marker, an imaging marker, or any combination of thereof. In certain embodiments, the inter-spacer distance is in the range of 50 µm to 120 µm. In certain embodiments, the inter-spacer distance is in the range of 120 µm to 200 µm (micron). In certain embodiments, the inter-spacer distance is substantially periodic. In certain embodiments, the spacers are pillars with a cross-sectional shape selected from round, polygonal, circular, square, rectangular, oval, elliptical, or any superpostional combination thereof. In certain embodiments, the spacers have a pillar shape and have a substantially flat top surface, wherein, for each spacer, the ratio of the lateral dimension of the spacer to its height is at least 1. In certain embodiments, each spacer has the ratio of the lateral dimension of the spacer to its height is at least 1. In certain embodiments, the minimum lateral dimension of the spacer is less than or substantially equal to the minimum dimension of an analyte in the sample. In certain embodiments, wherein the minimum lateral dimension of spacer is in the range of 0.5 µm to 100 µm, or 0.5 µm to 10 µm. In certain embodiments, the spacers have a pillar shape, and the sidewall corners of the spacers have a round shape with a radius of curvature at least 1 µm. In certain embodiments, the spacers have a density of at least 100/mm$^2$. In certain embodiments, the spacers have a density of at least 1,000/mm$^2$. In certain embodiments, at least one of the plates is transparent. In certain embodiments, at least one of the plates is made from a flexible polymer. In certain embodiments, a pressure that compresses the plates, the spacers are not compressible and/or, independently, only one of the plates is flexible. In certain embodiments, the flexible plate has a thickness in the range of 10 µm to 200 µm. In certain embodiments, the first and second plates are connected and are configured to be changed from the open configuration to the closed configuration by folding the plates. In certain embodiments, the first and second plates are connected by a hinge and are configured to be changed from the open configuration to the closed configuration by folding the plates along the hinge. In certain embodiments, wherein the first and second plates are connected by a hinge that is a separate material to the plates, and are configured to be changed from the open configuration to the closed configuration by folding the plates along the hinge. In certain embodiments, the first and second plates are made in a single piece of material and are configured to be changed from the open configuration to the closed configuration by folding the plates. In certain embodiments, the device is configured to analyze the sample in 60 seconds or less. In certain embodiments, at the closed configuration, the final sample thickness device is configured to analyze the sample in 60 seconds or less. In certain embodiments, at the closed configuration, the final sample thickness device is configured to analyze the sample in 10 seconds or less. In certain embodiments, the dry binding site comprises a capture agent. In certain embodiments, the dry binding site comprises an antibody or nucleic acid. In certain embodiments, the releasable dry reagent is a labeled reagent. In certain embodiments, the releasable dry reagent is a fluorescently-labeled reagent. In certain embodiments, the releasable dry reagent is a fluorescently-labeled antibody. In certain embodiments, the detector is an optical detector that detects an optical signal. In certain embodiments, the detector is an electric detector that detects electrical signal. In one aspect, the present invention provides a system for rapidly analyzing a sample using a mobile phone comprising: (a) a device of any prior embodiment; (b) a mobile communication device comprising: (i) one or a plurality of cameras for the detecting and/or imaging the sample; (ii) electronics, signal processors, hardware and software for receiving and/or processing the detected signal and/or the image of the sample and for remote communication; and (c) a light source from either the mobile communication device or an external source; wherein the detector in the devices or methods can be provided by the mobile communication device, and detects an analyte in the sample at the closed configuration. In certain embodiments, the system further comprising: (d) a housing configured to hold the sample and to be mounted to the mobile communication device. In certain embodiments, one of the plates has a binding site that binds an analyte, wherein at least part of the uniform sample thickness layer is over the binding site, and is substantially less than the average lateral linear dimension of the binding site.

In certain embodiments, the housing comprises optics for facilitating the imaging and/or signal processing of the sample by the mobile communication device, and a mount configured to hold the optics on the mobile communication device. In certain embodiments, an element of the optics in the housing is movable relative to the housing. In certain embodiments, the mobile communication device is configured to communicate test results to a medical professional, a medical facility or an insurance company. In certain embodiments, the mobile communication device is further configured to communicate information on the test and the subject with the medical professional, medical facility or insurance company. In certain embodiments, the mobile communication device is further configured to communicate information of the test to a cloud network, and the cloud network process the information to refine the test results. In certain embodiments, the mobile communication device is further configured to communicate information of the test and the subject to a cloud network, the cloud network process the information to refine the test results, and the refined test results will send back the subject. In certain embodiments, the mobile communication device is configured to receive a prescription, diagnosis or a recommendation from a medical professional. In certain embodiments, the mobile communication device is configured with hardware and software to: (a) capture an image of the sample; (b) analyze a test location and a control location in the image; and (c) compare a value obtained from analysis of the test location to a threshold value that characterizes the rapid diagnostic test. In certain embodiments, at least one of the plates comprises a storage site in which assay reagents are stored. In certain embodiments, at least one of the cameras reads a signal from the device. In certain embodiments, the mobile communication device communicates with the remote location via a WIFI or cellular network. In certain embodiments, the mobile communication device is a mobile phone (e.g., iPhone 6S or iPhone 10). In one aspect, the present invention provides a method for rapidly analyzing an analyte in a sample using a mobile phone, comprising: (a) depositing a sample on the device of any prior system embodiment; (b) assaying an analyte in the sample deposited on the device to generate a result; and (c) communicating the result from the mobile communication device to a location remote from the mobile communication device. In certain embodiments, the present method further comprises: analyzing the results at the remote location to provide an analyzed result; and communicating the analyzed result from the remote location to the mobile communication device. In certain embodiments, the analysis is done by a medical professional at a remote location. In certain embodiments, the mobile communication device receives a prescription, diagnosis or a recommendation from a medical professional at a remote location. In certain embodiments, the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample. In certain embodiments, the first plate has on its surface at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample. In certain embodiments, the analyte assay area is between a pair of electrodes. In certain embodiments, the assay area is defined by a patch of dried reagent. In certain embodiments, the assay area binds to and immobilizes the analyte. In certain embodiments, the assay area is defined by a patch of binding reagent that, upon contacting the sample, dissolves into the sample, diffuses in the sample, and binds to the analyte. In certain embodiments, the area-determination device is a camera. In certain embodiments, the area-determination device comprises an area in the sample contact area of a plate, wherein the area is less than 1/100, 1/20, 1/10, 1/6, 1/5, 1/4, 1/3, 1/2, 2/3 of the sample contact area, including intermediate values and ranges. In certain embodiments, the area-determination device comprises a camera and an area in the sample contact area of a plate, wherein the area is in contact with the sample. In certain embodiments, the deformable sample comprises a liquid sample. In certain embodiments, the imprecision force has a variation at least 30% of the total force that actually is applied. In certain embodiments, the imprecision force has a variation at least 20%, 30%, 40%, 50%, 60, 70%, 80%, 90% 100%, 150%, 200%, 300%, 500%, including intermediate values and ranges, of the total force that actually is applied. In certain embodiments, the spacers have a flat top. In certain embodiments, the device is further configured to have, after the pressing force is removed, a sample thickness that is substantially the same in thickness and uniformity as that when the force is applied. In certain embodiments, the imprecise force is provided by human hand. In certain embodiments, the inter spacer distance is substantially constant. In certain embodiments, the inter spacer distance is substantially periodic in the area of the uniform sample thickness area. In certain embodiments, the multiplication product of the filling factor and the Young's modulus of the spacer is 2 MPa or larger. In certain embodiments, the force is applied by hand directly or indirectly. In certain embodiments, the force applied is in the range of 1 N to 20 N. In certain embodiments, the force applied is in the range of 20 N to 200 N. In certain embodiments, the highly uniform layer has a thickness that varies by less than 15%, 10%, or 5% of an average thickness. In certain embodiments, the imprecise force is applied by pinching the device between a thumb and forefinger. In certain embodiments, the predetermined sample thickness is larger than the spacer height. In certain embodiments, the device holds itself in the closed configuration after the pressing force has been removed. In certain embodiments, the uniform thickness sample layer area is larger than that area upon which the pressing force is applied. In certain embodiments, the spacers do not significantly deform during application of the pressing force. In certain embodiments, the pressing force is not predetermined beforehand and is not measured. In certain embodiments, the fluidic sample is replaced by a deformable sample and the embodiments for making at least a part of the fluidic sample into a uniform thickness layer can make at least a part of the deformable sample into a uniform thickness layer.

In certain embodiments, the inter spacer distance is periodic. In certain embodiments, the spacers have a flat top. In certain embodiments, the inter spacer distance is at least two times large than the size of the targeted analyte in the sample.

Compressed Regulated Open Flow" (CROF)

In assaying, a manipulation of a sample or a reagent can lead to improvements in the assaying. The manipulation includes, but not limited to, manipulating the geometric shape and location of a sample and/or a reagent, a mixing or a binding of a sample and a reagent, and a contact area of a sample of reagent to a plate. Many embodiments of the present invention manipulate the geometric size, location, contact areas, and mixing of a sample and/or a reagent using a method, termed "compressed regulated open flow (CROF)", and a device that performs CROF. The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates. The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer. In certain embodiments, the method of CROF, comprises: (a) obtaining a sample, that is flowable; (b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface; (c) depositing, when the plates are configured in an open configuration, the sample on one or both of the plates; wherein the open configuration is a configuration in which the two plates are either partially or completely separated apart and the spacing between the plates is not regulated by the spacers; and (d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices/apparatus, systems, and methods herein disclosed are defined in the current application, or in PCT Application (designating U.S.) Nos. PCT/US2016/045437 and PCT/US0216/051775, respectively filed Aug. 10, 2016 and Sep. 14, 2016, U.S. Provisional Application Nos. 62/456,065, filed Feb. 7, 2017; 62/456,287, filed Feb. 8, 2017; and 62/456,504, filed Feb. 8, 2017, all of which are incorporated herein in their entirety for all purposes. The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the abovementioned Ser. No. 62/456,065.

(2) Sample

The devices/apparatus, systems, and methods herein disclosed can be applied to manipulation and detection of various types of samples. The samples are herein disclosed, listed, described, and/or summarized in the abovementioned applications (see definitions (1)). The devices, apparatus, systems, and methods herein disclosed can be used for samples such as but not limited to diagnostic samples, clinical samples, environmental samples and foodstuff samples. The types of sample include but are not limited to the samples listed, described and/or summarized in the abovementioned PCT applications (see definitions (1)).

The subject devices, apparatus, systems, and methods can be used to analyze any volume of the sample. Examples of the volumes include, but are not limited to, about 10 mL or less, 5 mL or less, 3 mL or less, 1 microliter (μL, also "uL" herein) or less, 500 μL or less, 300 μL or less, 250 μL or less, 200 μL or less, 170 μL or less, 150 μL or less, 125 μL or less, 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 pL or less, 1 pL or less, including intermediate values and ranges. In some embodiments, the volume of the sample includes, but is not limited to, about 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 pL or less, 1 pL or less, or a range between any two of the values. In some embodiments, the volume of the sample includes, but is not limited to, about 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 pL or less, 1 pL or less, including intermediate values and ranges. In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw. In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in the abovementioned PCT applications (see definitions (1)). The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample. The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate. The term "inner surface" or "sample surface" of a plate in a QMAX card refers to the surface of the plate that touches the sample, while the other surface (that does not touch the sample) of the plate is termed "outer surface". The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing. The term "area" of an object in a QMAX process refers to, unless specifically stated, the area of the object that is parallel to a surface of the plate. For example, spacer area is the area of the spacer that is parallel to a surface of the plate. The term of QMAX card refers the device that perform a QMAX (e.g., CROF) process on a sample, and have or not have a hinge that connect the two plates. The term "QMAX card with a hinge and "QMAX card" are interchangeable. The term "angle self-maintain", "angle self-maintaining", or "rotation angle self-maintaining" refers to the property of the hinge, which substantially maintains an angle between the two plates, after an external force that moves the plates from an initial angle into the angle is removed from the plates. In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate. In the QMAX assay platform, a QMAX card uses two plates to manipulate the shape of a sample into a thin layer (e.g., by compressing). In certain embodiments, the plate manipulation needs to change the relative position (termed: plate configuration) of the two plates several times by human hands or other external forces. There is a need to design the QMAX card to make the hand operation easy and fast. In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 μm. In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 μm thick PMA), such separation can be difficult to perform by hand. The present invention intends to provide the devices and methods that make the operation of certain assays, such as the QMAX card assay, easy and fast. In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates. In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof. In essence, the term "spacers" or "stoppers" refer to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes. The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

In some embodiments, human hands can be used to press the plates into a closed configuration; In some embodiments, human hands can be used to press the sample into a thin layer. The manner in which hand pressing is employed is described and/or summarized in PCT Application (designating U.S.) Nos. PCT/US2016/045437 filed Aug. 10, 2016, and PCT/US0216/051775, filed Sep. 14, 2016, and in U.S. Provisional Application Nos. 62/431,639, filed Dec. 9, 2016, 62/456,287, filed Feb. 8, 2017, 62/456,065, filed Feb. 7, 2017, 62/456,504, filed Feb. 8, 2017, and 62/460,062, filed Feb. 16, 2017, which are all incorporated by reference in their entirety. In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g., less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, respectively filed Aug. 10, 2016 and Sep. 14, 2016, and US Provisional Application Nos. 62/431,639, filed Dec. 9, 2016, 62/456,065, filed Feb. 7, 2017, and 62/456,287 and 62/456, 504, filed Feb. 8, 2017, and 62/539,660, filed Aug. 1, 2017, all of which are incorporated herein in their entirety. In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in abovementioned PCT Applications (designating U.S.), and US Provisional Applications. In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g., a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device. In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in abovementioned PCT Applications (designating U.S.), and US Provisional Applications. In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing. In some embodiments, the smartphone comprises a light source such as but not limited to LED (light emitting diode). In certain embodiments, the light source is used to provide illumination to the sample when the sample is positioned in the field of view of the camera (e.g., by an adaptor). In some embodiments, the light from the light source is enhanced, magnified, altered, and/or optimized by optical components of the adaptor. In some embodiments, the smartphone comprises a processor that is configured to process the information from the sample. The smartphone includes software instructions that, when executed by the processor, can enhance, magnify, and/or optimize the signals (e.g., images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof. In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in abovementioned PCT Applications (designating U.S.), and US Provisional Applications.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in abovementioned PCT Applications (designating U.S.), and US Provisional Applications. In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth- alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethyl-coumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-, 2'-disulfonic acid; 4,4'-diisothiocyanatostilbene-2,2'-disulfonic acid; 5-(dimethylaminolnaphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino- -fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives:

6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from Aequoria victoria or a derivative thereof, e.g., a "humanized" derivative such as Enhanced GFP; a GFP from another species such as Renilla reniformis, Renilla mulleri, or Ptilosarcus guernyi; "humanized" recombinant GFP (hrGFP); any of a variety of fluorescent and colored proteins from Anthozoan species; combinations thereof; and the like. In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025., wherein the reading step d) includes obtaining a measure of the amount of the plurality of biomarkers in the sample, and wherein the amount of the plurality of biomarkers in the sample is diagnostic of a disease or condition. In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025. In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in abovementioned PCT Applications (designating U.S.), and US Provisional Applications. The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food. In any embodiment, the sample can be a diagnostic sample obtained from a subject, the analyte can be a biomarker, and the measured the amount of the analyte in the sample can be diagnostic of a disease or a condition. In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location. In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7. In any embodiment, the applying step b) can include isolating miRNA from the sample to generate an isolated miRNA sample, and applying the isolated miRNA sample to the disk-coupled dots-on-pillar antenna (QMAX device) array. In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition. In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6. In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition. In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025. In any embodiment, the method can include receiving or providing a report that indicates the safety or harmfulness for a subject to be exposed to the environment from which the sample was obtained. In any embodiment, the method can include sending data containing the measured amount of the environmental marker to a remote location and receiving a report that indicates the safety or harmfulness for a subject to be exposed to the environment from which the sample was obtained. In any embodiment, the QMAX device array can include a plurality of capture agents that each bind to an environmental marker selected from Table B8, and wherein the reading step d) can include obtaining a measure of the amount of the plurality of environmental markers in the sample. In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9. In any embodiment, the method can include receiving or providing a report that indicates the safety or harmfulness for a subject to consume the foodstuff from which the sample is obtained. In any embodiment, the method can include sending data containing the measured amount of the foodstuff marker to a remote location and receiving a report that indicates the safety or harmfulness for a subject to consume the foodstuff from which the sample is obtained. In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption. Also provided herein are kits that find use in practicing the devices, systems and methods in the present invention. The amount of sample can be about a drop of a sample. The amount of sample can be the amount collected from a pricked finger or fingerstick. The amount of sample can be the amount collected from a microneedle or a venous draw. A sample can be used without further processing after obtaining it from the source, or can be processed, e.g., to enrich for an analyte of interest, remove large particulate matter, dissolve or resuspend a solid sample, etc. Any suitable method of applying a sample to the QMAX device can be employed. Suitable methods can include using a pipet, dropper, syringe, etc. In certain embodiments, when the QMAX device is located on a support in a dipstick format, as described below, the sample can be applied to the QMAX device by dipping a sample-receiving area of the dipstick into the sample. A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention. Washing the QMAX device to remove unbound sample components can be done in any convenient manner, as described above. In certain embodiments, the surface of the QMAX device is washed using binding buffer to remove unbound sample components. Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045,437 and PCT/US0216/051775, respectively filed Aug. 10, 2016 and Sep. 14, 2016, and U.S. Provisional Application Nos. 62/456,065, filed Feb. 7, 2017,. 62/456,287, filed Feb. 8, 2017, and 62/456,504, filed Feb. 8, 2017, all of which are incorporated herein in their entirety. In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others. The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals. In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food. In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof. In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition. In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained. In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S Provisional Application Nos. 62/431,639 filed on Dec. 9, 2016 and 62/456,287 filed on Feb. 8, 2017, which are all hereby incorporated by reference by their entireties.

(12) Cloud

The devices/apparatus, systems, and methods herein disclosed can employ cloud technology for data transfer, storage, and/or analysis. The related cloud technologies are herein disclosed, listed, described, and/or summarized in abovementioned PCT Applications (designating U.S.), and US Provisional Applications. In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g., smartphone) can be connected to the cloud through any type of network, including a local area network (LAN) or a wide area network (WAN). In some embodiments, the data (e.g., images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud. The following examples are provided to illustrate certain particular features and/or embodiments. These Examples are provided for the purpose of illustration only and should not be construed to limit the invention to the particular features or embodiments described. Variations and equivalents, which would be within the understanding and technical competence of a skilled artisan are to be considered as falling within the scope of the invention.

EXAMPLES

Example 1

Referring to the Figures, FIG. 1 is an illustration showing the process steps for detecting C-Reactive Protein (CRP)

according to some embodiments of the present invention. In this study, we performed the process of staining for CRP using the following steps:

First, we obtained the QMAX device as a sample holder. The QMAX device was configured to hold a liquid sample that contains an analyte (e.g., CRP). The sample holder includes a first plate and a second plate.

Second, we conjugated a capturing agent (e.g., a CRP capturing antibody) to the micro/nanostructures (e.g., beads) that were immobilized in the sample holder (e.g., on the first plate) according to manufacturer's protocol, i.e., using the NHS activated beads (Pierce™, 10 μm in diameter) with the anti-CRP mouse monoclonal capture antibody (Fitzgerald). The antibody conjugated beads were blocked by 4% BSA in PBS at 4° C. overnight and washed with PBST 6 times prior to use.

Third, we coated the first plate (having 10 μm pillars) with 1 μL of beads (beads concentration $10^7$-$10^8$/mL) were dropped on an X-plate with 10 μm pillars and air dried at room temperature.

Fourth, we immobilized a detecting agent (e.g., a labeled anti-CRP antibody) in the sample holder (e.g., on the second plate). The capturing agent was configured to specifically bind to the analyte, and the detecting agent was configured to be diffusible in the sample and bind to a complex of the capturing agent and the analyte.

Fifth, we obtained 1 μL of fresh whole blood and 1 μL of Cy5-labeled anti-CRP mouse monoclonal detection antibody (Fitzgerald) and deposited the sample in the sample contact area. The sample was dropped onto the area of coated beads on the first plate and placed in contact with the capturing agent and the detecting agent in the sample holder.

Sixth, we gently pressed the first plate and the second plate to a closed configuration by compressing the sample into a thin layer and incubated the sample for a predetermined period of time (i.e., 30 seconds).

Seventh, we detected the analyte, without washing, by imaging the sample layer and detecting signals from the detecting agent that binds to the complex of the capturing agent and the analyte using iPhone 6S.

Example 2

Figure 2:
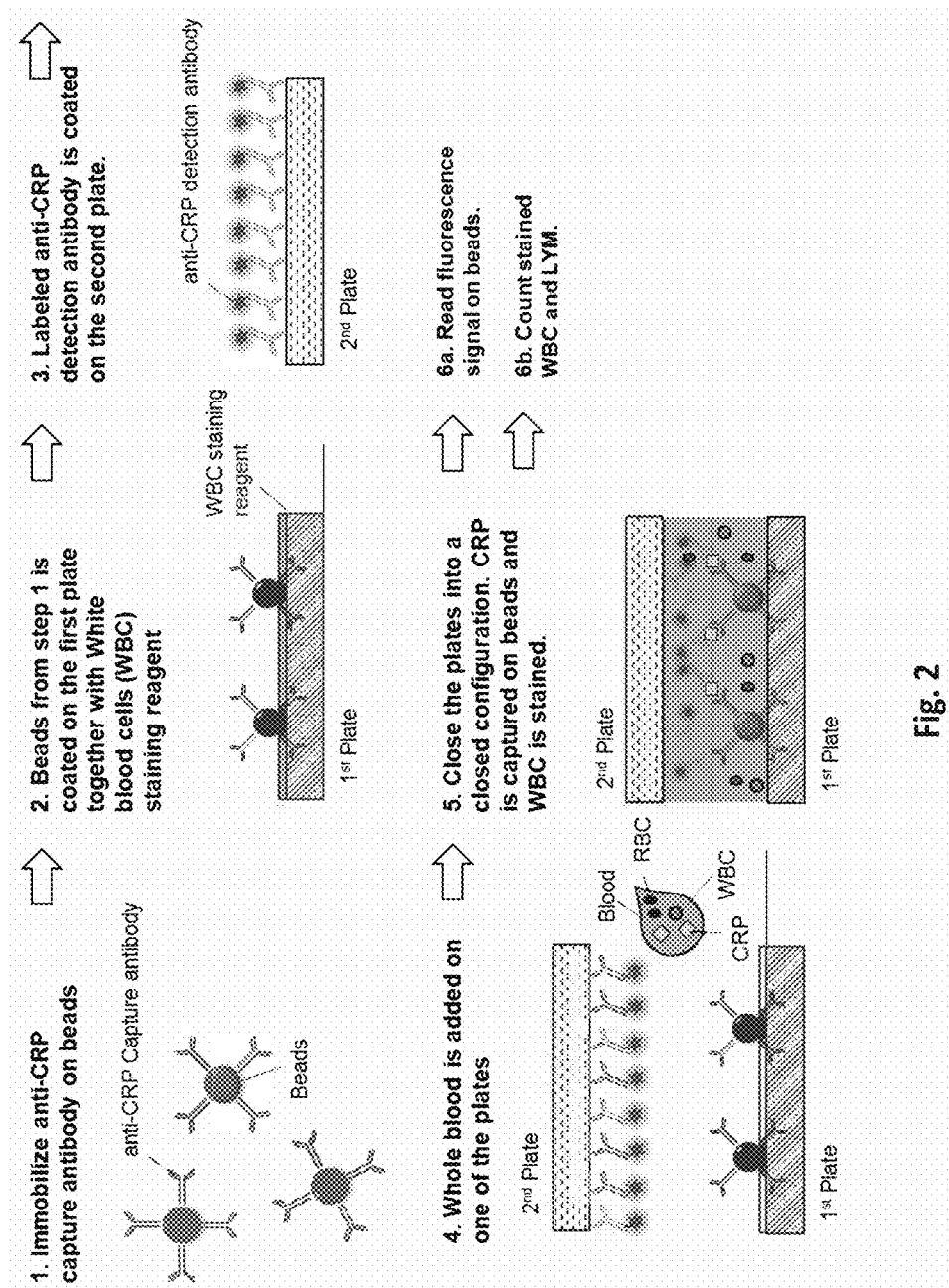
FIG. 2 provides a schematic showing the process for detecting C-Reactive Protein (CRP) (an acute phase reactant) and white blood cell (via staining).
Figure 3:
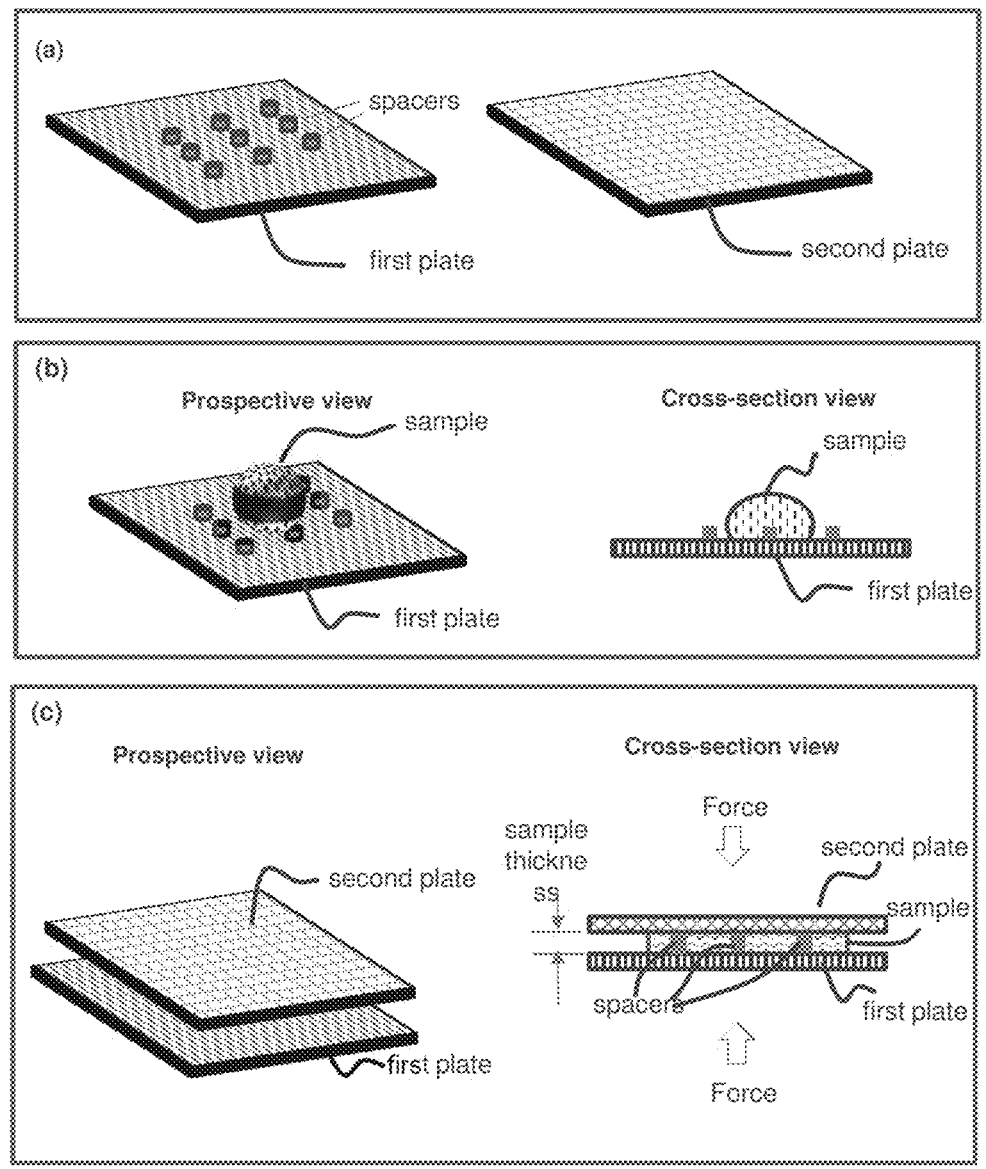
FIG. 3 is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate can have one or a plurality of binding sites and or storage sites (not shown).
Figure 4:
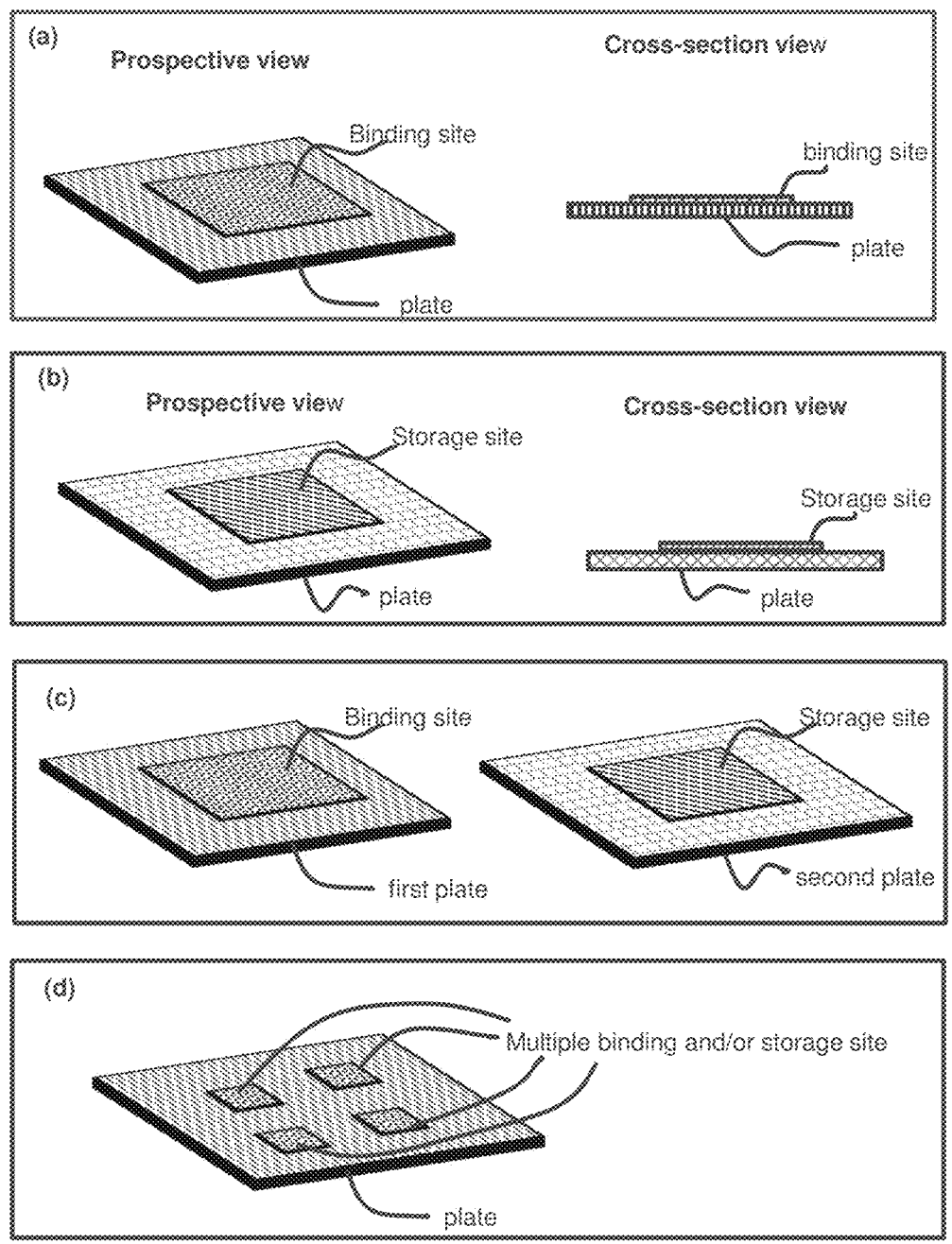
FIG. 4 illustrates plates with a binding site or a storage site. Panel (a) illustrates a plate having a binding site. Panel (b) illustrates a plate having a reagent storage site. Panel (c) illustrates a first plate having a binding site and a second plate having a reagent storage site. Panel (d) illustrates a plate having multiple sites (binding sites and/or storage site).

FIG. 2 illustrates the process for detecting C-Reactive Protein (CRP) and white blood cells (WBC) according to some embodiments of the present invention. In this study, we performed the process of staining for CRP and WBC using the following steps:

First, we obtained the QMAX device as a sample holder. The QMAX device was configured to hold a liquid sample that contains an analyte (e.g., CRP). The sample holder includes a first plate and a second plate.

Second, we conjugated a capturing agent (e.g., a CRP capturing antibody) to the micro/nanostructures (e.g., beads) that were immobilized in the sample holder (e.g., on the first plate) according to manufacturer's protocol, i.e., using the NHS activated beads (Pierce™, 10 μm in diameter) with the anti-CRP mouse monoclonal capture antibody (Fitzgerald). The antibody conjugated beads were blocked by 4% BSA in PBS at 4° C. overnight and washed by PBST for 6 times prior to use.

Third, we coated the first plate (having 10 μm pillars) with 1 μL of beads (beads concentration $10^7$-$10^8$/mL) and the white blood cell staining agent were dropped on X-plate with 10 μm pillars and air dried at room temperature.

Fourth, we immobilized a detecting agent (e.g., a labeled anti-CRP antibody) in the sample holder (e.g., on the second plate). The capturing agent was configured to specifically bind to the analyte, and the detecting agent was configured to be diffusible in the sample and bind to a complex of the capturing agent and the analyte.

Fifth, we obtained 1 μL of fresh whole blood and 1 μL of Cy5-labeled anti-CRP mouse monoclonal detection antibody (Fitzgerald) and deposited the sample in the sample contact area. The sample was dropped onto the area of coated beads on the first plate and placed in contact with the capturing agent and the detecting agent in the sample holder.

Sixth, we gently pressed the first plate and the second plate to a closed configuration by compressing the sample into a thin layer and incubated the sample for a predetermined period of time (i.e., 30 seconds).

Seventh, we detected the analyte (CRP) via the capturing antibody and the detection antibody, and the analyte (WBC) using the white blood cell stain (SYTO9), without washing, by imaging the sample layer and detecting signals from the detecting agent that binds to the complex of the capturing agent and the analyte using iPhone 6S.

Example 3

In this study, we prepared the first plate and the second plate as described in Example 1 above. Beads (10 μm in diameter) were conjugated with anti-CRP capture antibody and were dried on an X-plate with 10 μm spacer. Fresh whole blood and Cy5-labeled anti-CRP detection antibody (final concentration 25 μg/mL) were dropped on dried beads (volume ratio 9:1) and covered by a glass slide. After about 30 sec incubation, the images were taken by iPhone 6s.

Example 4

Figure 5:
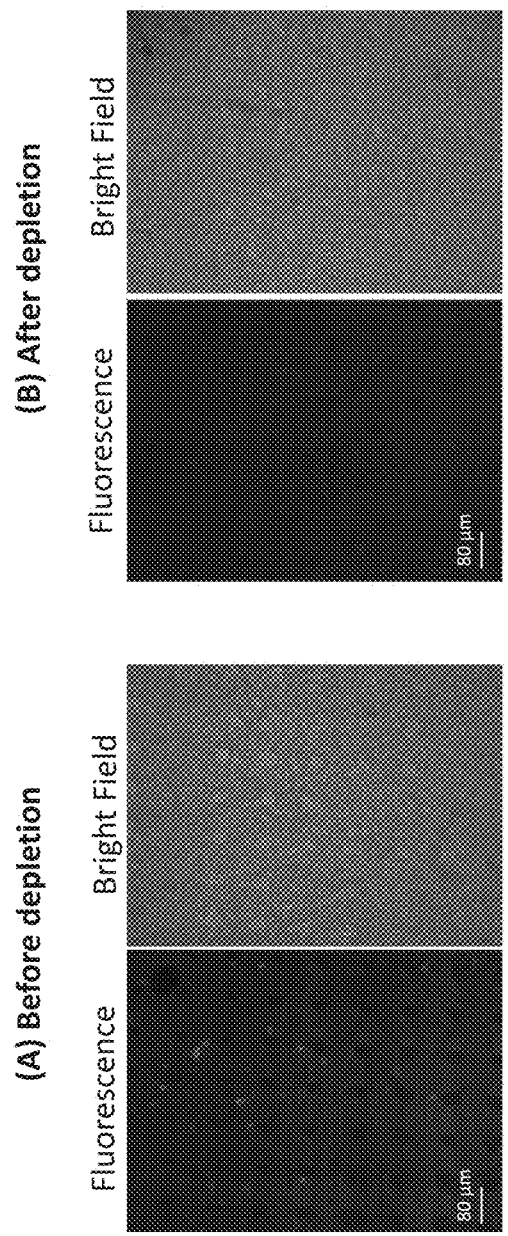
FIG. 5 shows exemplary pictures of CRP staining with the QMAX device before and after depletion of CRP protein in blood. The images were captured with the camera of a smart phone.

In this study, we depleted the endogenous CRP in the blood sample. We used 2 μm magnetic beads (Millipore) that were conjugated by anti-CRP antibody and incubated with whole blood for 2 hours at RT on a roller. The 2 μm magnetic beads with captured endogenous CRP were retained by magnet and CRP-depleted blood was transferred to a new tube. FIG. 5 shows exemplary pictures of CRP staining with the QMAX device before and after depletion. The images were captured with the camera of a smart phone. Beads (10 μm in diameter) conjugated with anti-CRP capture antibody were dried on x-plate with 10 μm spacer. Fresh whole blood (A) or CRP-depleted blood (B) and Cy5-labeled anti-CRP detection antibody (final concentration 25 μg/mL) were dropped on dried beads (volume ratio 9:1) and covered by glass slide. After about 30 sec incubation, the images were taken by iPhone 6s.

Example 5

In this study, we spiked varying amounts of CRP into CRP-depleted human whole blood.

Figure 6:
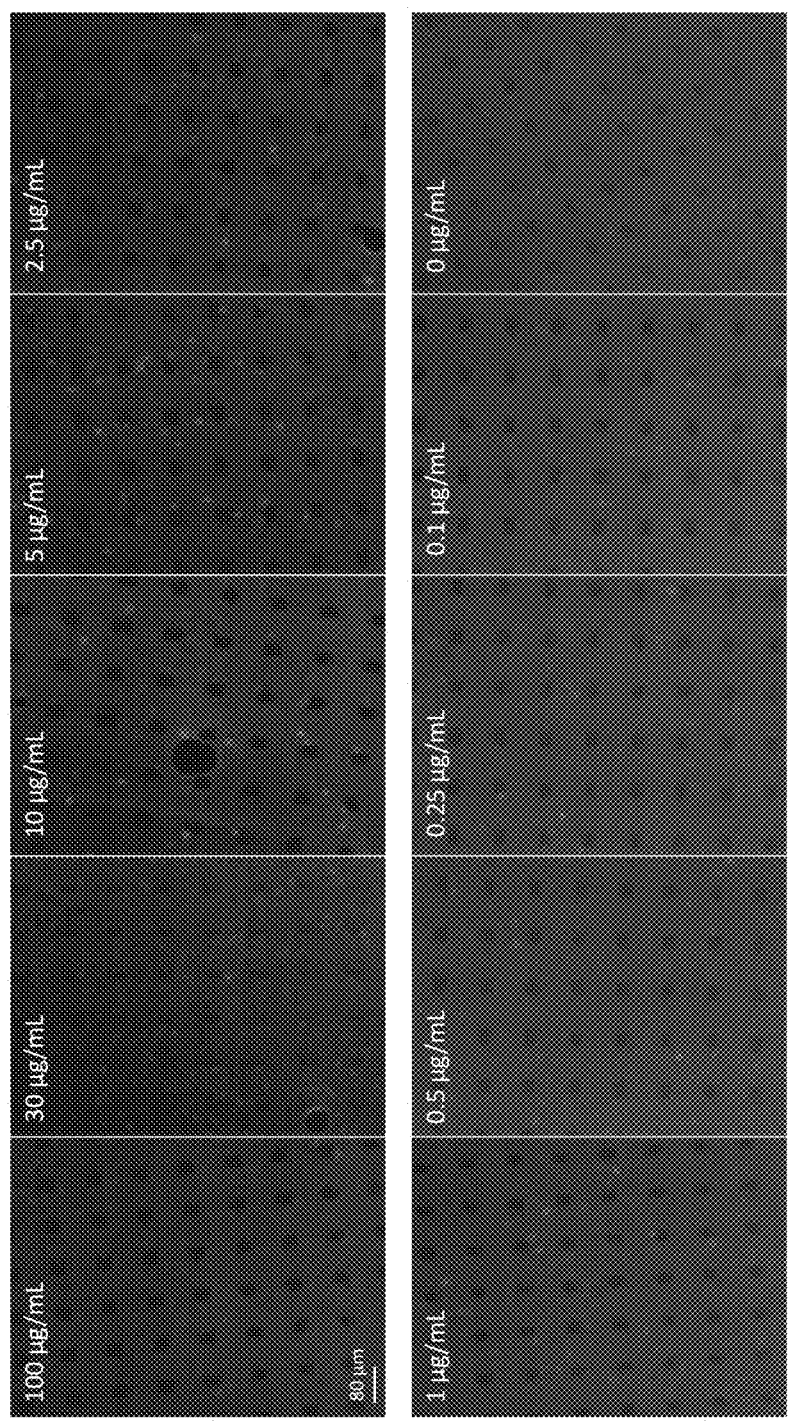
FIG. 6 shows exemplary pictures of CRP staining with the QMAX device wherein the sample is spiked with different concentrations of recombinant CRP in PBS buffer.

Known concentrations of recombinant CRP protein were spiked into CRP-depleted blood. 1 μL of spiked blood and 1 μL of Cy5-labeled anti-CRP mouse monoclonal detection antibody (Fitzgerald) were dropped onto the area of coated beads on the glass slide. The mix was immediately covered by the X-plate (second plate) with 10 μm pillars and incubated for 30 seconds. Without washing, we took the fluorescent images using iPhone 6s. FIG. 6 shows exemplary pictures of CRP staining with the QMAX device where the sample was spiked with different concentrations of CRP. Beads (10 μm in diameter) conjugated with anti-CRP capture antibody were dried on an X-plate with 10 μm spacer.

CRP-depleted blood spiked with different concentration of recombinant CRP and Cy5 labeled anti-CRP detection antibody (final concentration 25 μg/mL) were dropped on dried beads (volume ratio 9:1) and covered by glass slide. After 30 sec incubation, the images were taken by iPhone 6s. Hook effects are noted when CRP concentration was greater than 10 μg/mL. The limit of detection (LOD) was determined to be about 100 ng/mL in the spiking test in whole blood.

Example 6

Figure 7:
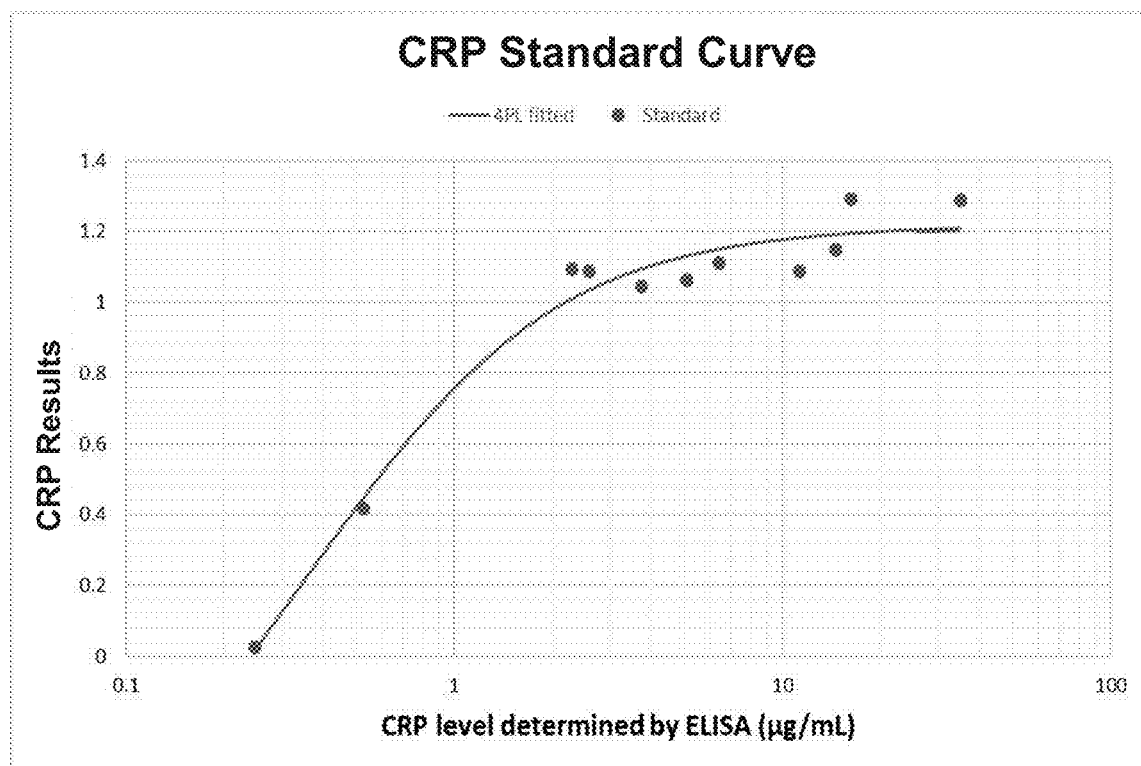
FIG. 7 shows a CRP Standard Curve. The standard curve was generated based on 11 human blood samples (dots). CRP was detected using the present QMAX device and a standard commercial ELISA (Abcam). The standard curve was calculated using 4-PL curve fitting (curve). The fitted curve has a $R^2$ value of 0.9643.
Figure 8:
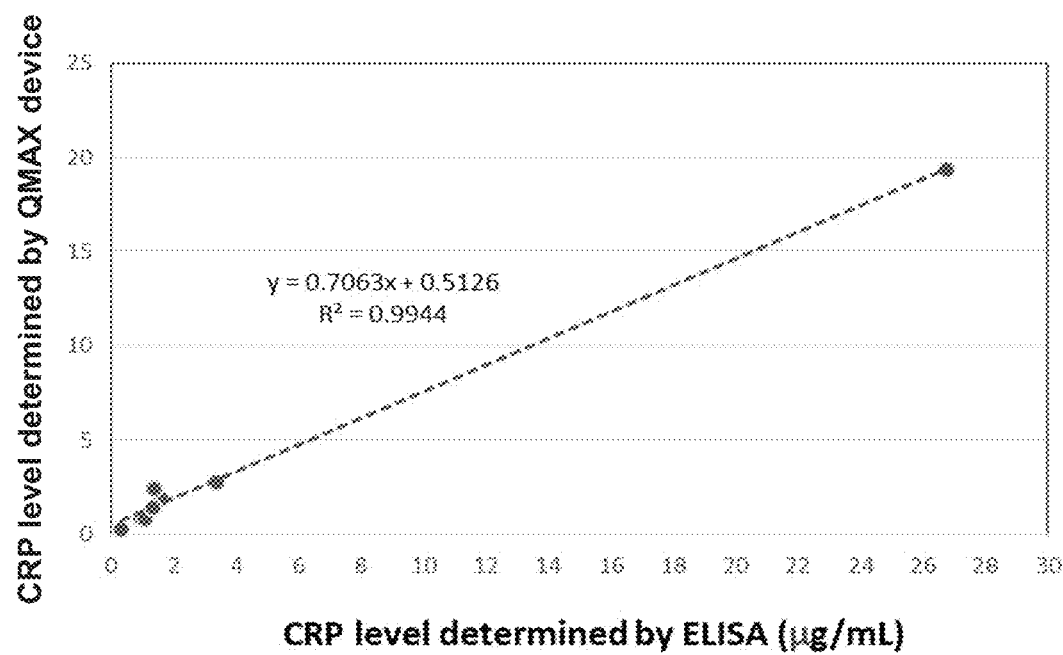
FIG. 8 shows CRP levels obtained using the QMAX device as compared to using the standard comercial ELISA (Abcam). 9 human blood samples (dots) were tested by both the present method and the commercial ELISA (Abcam). Their CRP levels were determined by interpolation from the standard curve (FIG. 7). The correlation between QMAX device and ELISA was plotted. $R^2$=0.9944 between the QMAX device and ELISA. Note that one sample (sample #36) was out of the standard curve range and thus not counted. Average accuracy of the present QMAX device as compared to that of the commercial ELISA (Abcam) is 109.1% (see Table 1).
Figure 9:
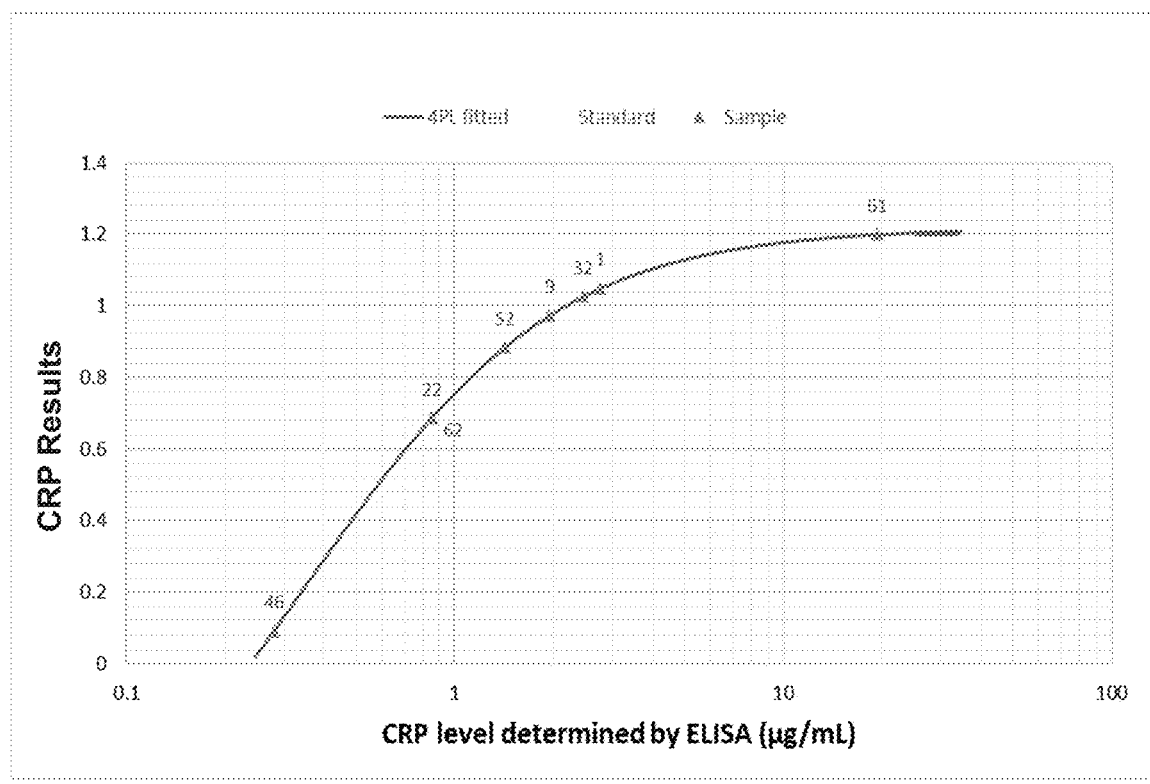
FIG. 9 shows CRP QMAX results of 9 unknown human blood samples interpolation from the standard curve (FIG. 7). Sample #36 is out of the standard curve range and not counted.
Figure 11:
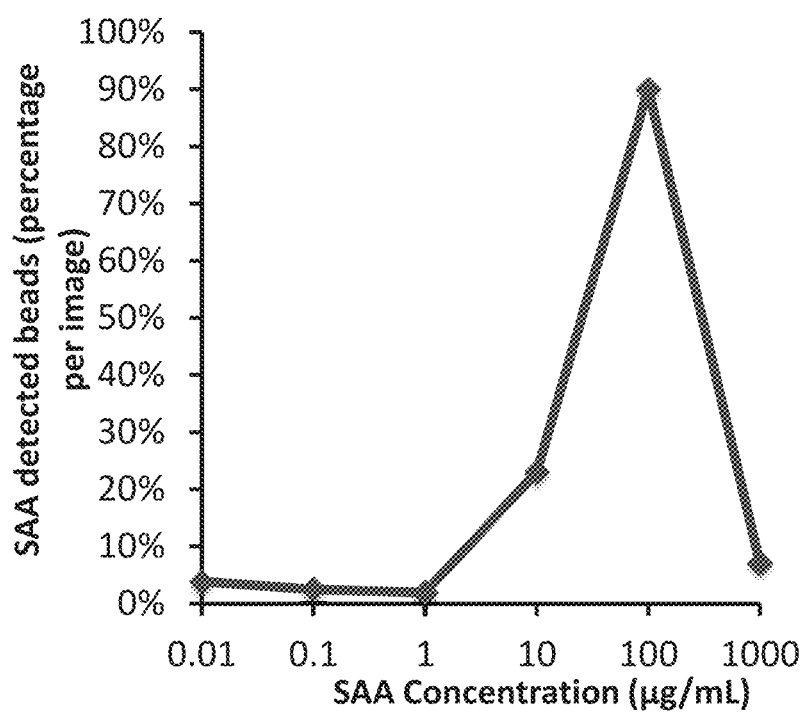
FIG. 11 shows the dose-dependent curve in detection of SAA. The limit of detection (LOD) for the SAA assay was 1 to 10 μg/mL.
Figure 12:
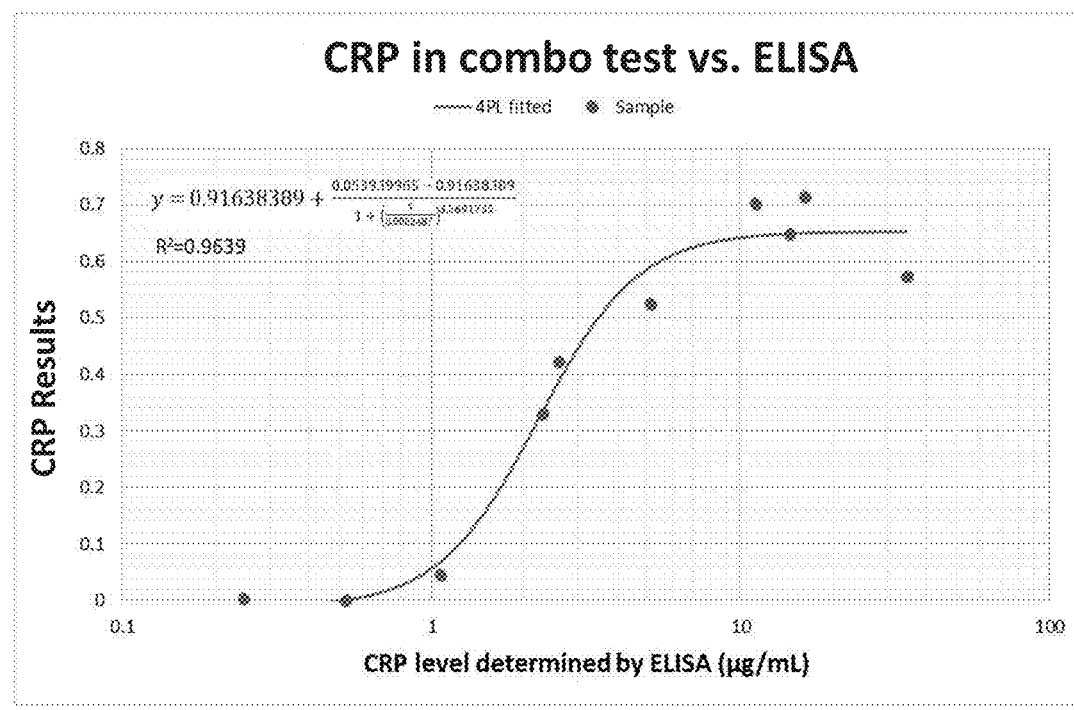
FIG. 12 shows CRP levels obtained using the QMAX device (when used in combination with WBC detection) as compared to using the standard comercial ELISA (Abcam). Nine human blood samples (dots) were tested by both the present method and the commercial ELISA (Abcam). Their CRP levels were determined by interpolation from the standard curve. The correlation between QMAX device and ELISA was plotted, and $R^2=0.9639$ between the QMAX device and ELISA. This result indicates that there is no interference from the WBC in CRP detection.

In this study, we adopted the method as described in Example 1. We obtained 11 blood samples (venous blood or finger-blood of patients at Hunterdon Hematology Oncology (Flemington, N.J., USA) and tested using the QMAX device. The results of the CRP detection using the QMAX device were compared to that of the gold standard ELISA test (SimpleStep ELISA® kits; Abcam) (following the manufacturer's instruction). As shown in FIG. 7, 11 blood samples (dots) were tested by the present QMAX device and the gold standard ELISA. A standard curve was generated using 4-PL curve fitting (curve line) and an $R^2$=0.9643.

and FIG. 11). As shown in FIG. 12, the correlation between the present assay and ELISA was plotted. $R^2$=0.9944 between the present assay and ELISA for 8 samples (sample #36 was out of BEST standard curve range and thus not counted). Average accuracy of the present assay compared to gold standard ELISA was found to be 109.1% (see Table 1).

Example 8

Figure 13:
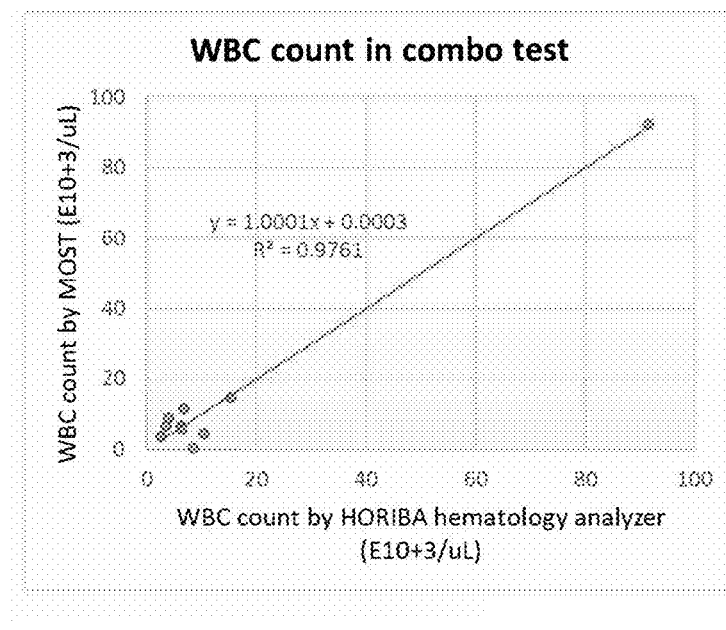
FIG. 13 shows the WBC count in CRP+WBC combo test. The $R^2$ value is 0.9761.

After the generation of the standard curve, we next obtained 9 new blood samples (dots) and tested the CRP concentration using the present QMAX device and compared that with the gold standard ELISA ((SimpleStep ELISA® kits; Abcam). As shown in FIG. 13, the CRP levels of the nine blood samples were determined by interpolation from the standard curve (FIG. 11).

Accompanying Table 2 summarizes the comparison between the present CRP test using QMAX device and ELISA (Abcam). Note that the present CRP test has high accuracy, sensitivity and specificity.

TABLE 2

| | Sample # | 46 | 1 | 22 | 61 | 9 | 62 | 32 | 52 | 36* | Average |
|---|---|---|---|---|---|---|---|---|---|---|---|
| Quantitative | BEST (μg/mL) | 0.28 | 2.77 | 0.85 | 19.37 | 1.94 | 0.85 | 2.46 | 1.42 | >22 | |
| | ELISA (ug/mL) | 0.3 | 3.34 | 0.94 | 26.73 | 1.58 | 1.07 | 1.34 | 1.3 | 10.31 | |
| | Accuracy[1] (%) | 94.6 | 83.0 | 90.6 | 72.5 | 122.9 | 79.7 | 184.3 | 108.7 | | 104.5 |
| | Intra-assay CV[2] (%) | 45.0 | 17.2 | 13.4 | 9.3 | 9.6 | 12.8 | 5.1 | 5.8 | | 14.8 |
| Qualitative | High CRP call by BEST (10 μg/mL as cut-off) | N | N | N | Y | N | N | N | N | Y | |
| | High CRP call by ELISA (10 μg/mL as cut-off) | N | N | N | Y | N | N | N | N | Y | |
| | Assay sensitivity for High CRP call | | | | | 100% (2/2) | | | | | |
| | Assay specificity for High CRP call | | | | | 100% (7/7) | | | | | |

*Sample #36 is out of BEST standard curve range (>22 ug/mL).
[1]Accuracy is defined as BEST results/ELISA results × 100.
[2]Intra-assay CV is defined as S.D./Mean × 100 in four replicates on one Q-card for each sample.

Accompanying Table 1 shows the limit of detection (LOD), accuracy, intra-assay (CV), assay sensitivity, assay specificity and $R^2$ of the present assay.

TABLE 1

| CRP test | |
|---|---|
| Sample type | Blood, serum, plasma |
| Time needed | ≤60 s |
| Limit of detection (LoD) | 30 ng/mL |
| Dynamic range | 30 ng/mL-22 μg/mL |
| Accuracy (n = 8) | 104.5% |
| Intra-assay CV (n = 20) | 14.8% |
| $R^2$ against gold standard (n = 8) | 0.9944 |
| Assay sensitivity (Qualitative, using 10 μg/mL as cut-off) (n = 9) | 100% |
| Assay specificity (Qualitative, using 10 μg/mL as cut-off) (n = 9) | 100% |

Example 7

In this study, the CRP levels were determined by interpolation from the standard curve (described in Example 6

Example 9

*Sample #36 is out of BEST standard curve range (>22 ug/mL).
[1]Accuracy is defined as BEST results/ELISA results×100.
[2]Intra-assay CV is defined as S. D./Mean×100 in four replicates on one Q-card for each sample.

Example 10

In this study, we prepared the first plate and the second plate as described in Example 1. Beads (10 μm in diameter) were conjugated with antibody against serum amyloid A (anti-SAA) capture antibody and were dried on x-plate with 10 μm spacer. Fresh whole blood and Cy5-labeled anti-SAA detection antibody (final concentration 25 μg/mL) were dropped on dried beads (volume ratio 9:1) and covered by glass slide. The whole blood was pre-treated with 5 mg/mL Zwittergent for 30 seconds to remove the RBC. After ~3 min incubation, the images were taken by iPHONE 6s. Phone parameters: ISO 100; speed ⅓ for FL & ¹⁄₄₀ for BF; WB 5500K; Zoom 3×.

Figure 10:
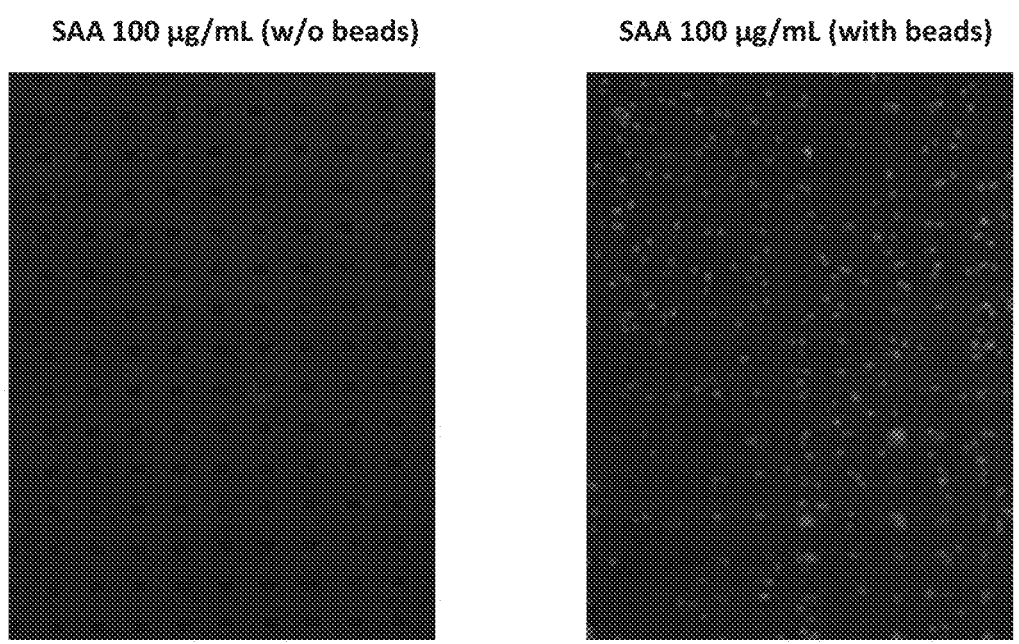
FIG. 10 shows the criticality of the beads used in detection of acute phase reactant (e.g., SAA).

FIG. 10 shows exemplary pictures of SAA staining with the QMAX device in fluorescence field. Without beads a fluorescence signal could not be measured. Only when the anti-SAA capture antibody was conjugated to the beads then a fluorescence signal could be measured. This result indicates that it is critical to conjugate the anti-SAA capture antibody to the beads. The images were captured with the camera of a smart phone. In a preliminary study, we spiked varying concentrations (1 μg/mL to 500 μg/mL) of human recombinant SAA in human whole blood. In this study, we observed that our QMAX device assay could detect SAA concentrations from 10 μg/mL to 500 μg/mL. We noted that the present SAA assay has a minimum hook effect (or the prozone effect) which is a type of interference that plagues common immunoassays resulting in false negatives or inaccurately low results.

Example 11

In this study, we followed the protocol as detailed in Example 2 and used the QMAX device to detect CRP and WBC (duplex test or combo test).

FIG. 12 shows the correlation of CRP levels (from ten (10) human blood samples) as measured by our QMAX device and the gold standard ELISA. The correlation curve has a $R^2$ value of 0.9639, indicating a good correlation between QMAX device and the gold standard ELISA.

FIG. 13 shows the comparison of the WBC counts in the same ten (10) human blood samples as measured by QMAX device and the hematology analyzer. The R2 value (0.9761) also indicates a good correlation between QMAX device and the gold standard hematology analyzer.

Accompanying Table 3 shows the characteristic features of our CRP and WBC combo test (using the QMAX device). The LOD for CRP is 30 ng/mL, $R^2$ for CRP is 0.9639 and $R^2$ for WBC is 0.9761.

TABLE 3

| CRP + WBC combo test | |
|---|---|
| Sample type | Blood |
| Time needed | ≤60 s |
| Limit of detection (LoD) for CRP | 30 ng/mL |
| Dynamic range for CRP | 30 ng/mL-22 μg/mL |
| $R^2$ for CRP (n = 10) | 0.9639 |
| $R^2$ for WBC (n = 10) | 0.9761 |

Example 12

In this study, we used the FL-Cy3 to detect CRP (1 μg/mL) and FL-Cy5 to detect SAA (100 μg/mL). With the two fluorescence, we evaluated the specificity of fluorescent staining for CRP and SAA. For CRP, we used the Cy3 as the fluorescent tag on the detection antibody. For SAA, we used the Cy5 as the fluorescent tag on the detection antibody.

Figure 14:
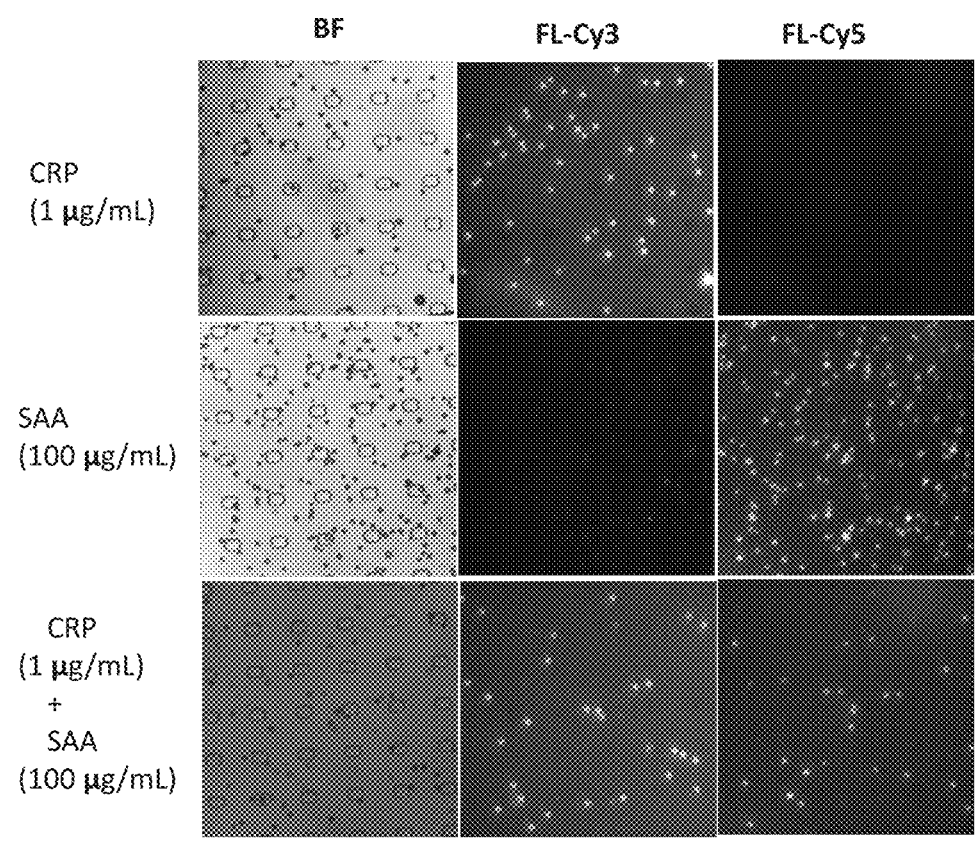
FIG. 14 shows the specificity of Cy3 to detect CRP and Cy5 to detect SAA. Note that there is no fluorescent Cy3 signal leakage under Cy5 wavelength or fluorescent Cy5 signal leakage under Cy3 wavelength, indicating the feasibility of the duplex detection assay using both the Cy3 and Cy5 at the same time.

As shown in FIG. 14, the bright field pictures show the presence of the beads in all three assays (i.e., CRP, SAA and CRP+SAA). For the CRP assay, the Fl-Cy3 only appeared under the Cy3 channel, but not appeared under the Cy5 channel. For SAA assay, the Fl-Cy5 only appeared under the Cy5 channel, but not appeared under the Cy3 channel. For the CRP +SAA duplex assay (i.e., using both Cy3-conjugated detection antibody (for CRP) and Cy5-conjugated detection antibody (for SAA), we observed fluorescence under both the Cy3 channel and Cy5 channel Accompanying Table 4 shows the specificity of capture antibody and detection antibody. There is no cross reactivity in the CRP assay (i.e., CRP capture mAb and CRP detection nmAb) for SAA detection or vice versa.

This result indicates the feasibility of using both Cy3 and Cy5 fluorescent tags for the CRP+SAA duplex assay. There is no overlap in the fluorescent signals under Cy3 and Cy5 channels. There is no cross interference between the FL-Cy3 and FL-Cy5. The present assay can simultaneously detect CRP and SAA.

TABLE 4

| Testing # | Capture mAb | Detection mAb | Antigen | Activity |
|---|---|---|---|---|
| 1 | CRP | SAA | — | No |
| 2 | SAA | CRP | — | No |
| 3 | CRP | CRP | SAA (100 μg/mL) | No |
| 4 | SAA | SAA | CRP (1 μg/mL) | No |
| 5 | CRP + SAA | CRP + SAA | CRP (1 μg/mL) | Yes |
| 6 | CRP + SAA | CRP + SAA | SAA (100 μg/mL) | Yes |
| 7 | CRP | CRP | CRP (1 μg/mL) | Yes |
| 8 | SAA | SAA | SAA (100 μg/mL) | Yes |
| 9 | CRP | CRP | — | No |
| 10 | SAA | SAA | — | No |

Example 13

Table 4 shows there is no cross-reactivity or interference between CRP assay and SAA assay. In this study. for individual detection of CRP, we used anti-CRP capture antibody beads in combination with CRP detection antibody. For individual detection of SAA, we used anti-SAA capture antibody beads in combination with SAA detection antibody. For simultaneous detection of both CRP and SAA, we mixed anti-CRP capture antibody beads and anti-SAA capture antibody beads (1:1 ratio), and mixed the CRP detection antibody and SAA detection antibody (1:1 ratio).

Experimental Protocols (1) Conjugation of a Capture Antibody for CRP to Beads

COOH activated polystyrene beadsffig (Thermo Fisher Scientific, 10 μm in diameter) are conjugated to an anti-CRP mouse monoclonal antibody (i.e., capture antibody) (Fitzgerald) according to manufacturer's protocol. Briefly, COOH activated polystryrene beads at the concentration of 20 mg/mL in MES (pH 6.0) are incubated with 10 mg/mL EDC and capture antibody for 2 hours at room temperature. After incubation, the excessive EDC and unbound antibody are washed using PBS.

(2) Conjugation of a Capture Antibody for SAA to Beads

For SAA, the anti-SAA mouse monoclonal antibody (VSA25) (i.e., capture antibody) was obtained from Hytest Ltd (catalog #4SA11). Polystyrene beads (PS beads) (Bangs Lab) (9.94 μm) conjugation with SAA antibody is performed using the following procedure.

1. Resuspend 10 μm PS beads in bottle by vertexing and shaking gently, Pipette 50 μl of PS beads into a 2 ml protein low binding Eppendorf tube.
2. Add 150 μl25 mM MES, pH 6.0 to the tube. Spin down the tube for 2 min at 5500 RCF.
3. Wash the beads 3× with 500 ul 25 mM MES, pH 6.0. Pipette off the supernatant carefully, leaving beads undisturbed.
4. Prepare 20 mg/ml EDCA and 28 mg/ml NHS in 25 mM MES, pH 6.0, respectively.

5. Add 75 μL each into the beads tube. Mix on the lowest vortex setting for 30 min at RT.
6. Spin down the beads after activation. Pipette off the supernatant solution.
7. Add 100 μL SAA antibody (100 μg in total) to the tube. Mix on the lowest vortex setting for 2 h at RT.
8. After two hours incubation, centrifuge down the beads at 5500 RCF×2 mins.
9. Pipette off the supernatant solution, add 300 μL of Quench Buffer (100 mM Tris-HCl, 150 mM NaCl, pH 8.0) vortex vigorously for 30 seconds. Centrifuge. Remove the buffer with a pipette and discard.
10. Wash the beads for an additional 4 times using 500 μL of Quench Buffer (100 mM Tris-HCl, 150 mM NaCl, pH 8.0) as described in step 9.
11. Add 500 μL of Quench Buffer (100 mM Tris-HCl, 150 mM NaCl, pH 8.0) and incubate for 30 min at room temperature. Remove the buffer with a pipette and discard.
12. Wash the beads 3 times with 1×PBS, then resuspend the beads in 500 μL 1% casein (blocking agent) in PBS, rotating overnight at 4° C.
13. Next day, wash beads 3 times with 1×PBST, then suspend beads in 500 μL of 1× PBST (3) Blocking of Beads The non-specific binding sites on the antibody conjugated beads are blocked using 4% BSA in PBS at 4° C. overnight following by washing with PBST (6 times) prior to use.

(4) Coating First Plate

4 μL of beads from Step 2 (beads concentration $10^7$-$10^8$/mL) together with red blood cell (RBC) lysis reagent (Zwittergent) (3 mg/mL) is printed by Biodot fluid dispenser on the first plate with 10 μm pillars and air dried at room temperature for 20 min.

(5) Labeling of Detection Antibody

An anti-CRP mouse monoclonal detection antibody (Fitzgerald) is labeled by Cy5 using Cy5 labeling kit (Abcam) according to the manufacturer's protocol. Briefly, 100 μg detection antibody is conjugated to Cy5-NHS provided in the kit and excessive Cy5-NHS is quenched before use. Cy3 fluorescence is conjugated to anti-CRP using the same protocol. For SAA, the anti-SAA mouse monoclonal detection antibody (Hytest Ltd) (catalog 4VS4) was similarly conjugated with Cy5 fluorescence dye according to the manufacturer's protocol.

(6) Coating Second Plate

4 μL of labeled antibody with a concentration of 10 μg/mL with red blood cell (RBC) lysis reagent (Zwittergent) (3 mg/mL) is printed by Biodot fluid dispenser on the second plate (substrate plate) and air dried at room temperature for 20 min.

(7) White Cell Staining Reagent

SYTO 9 green fluorescent nucleic acid stain (Thermo Fisher) is used as a white blood cell staining reagent in our study.

(8) Homogenous Assay

4 μL of blood is dropped onto the area of coated beads on the second plate then immediately covered by first plate with 10 μm pillars and incubated for 60 seconds.

(9) Spiking

In spiking experiments, recombinant proteins for human CRP (Fitzgerald Industries International (catalog no. 30-AC05) or human serum amyloid A (Fitzgerald Industries International (catalog no. 30-1380) were used to spike into human whole blood prior to the detection assay using QMAX card.

(10) Imaging

Without washing, the beads on Q-card are illuminated by a laser device and the fluorescent images were taken by iPhone 6s.

(11) Reading and Analysis

Beads signal and the signal of area around each bead (background signal) is measured. The true assay signal is calculated by subtracting background signal from bead signal and averaged for each card.

Additional Notes

Further examples of inventive subject matter according to the present disclosure are described in the following paragraphs. It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents. As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function can additionally or alternatively be described as being operative to perform that function. As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure. As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") can refer to A alone, B alone, or the combination of A and B. As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entities can optionally be present other than the entity specifically identified by the "and/or" clause, whether related or unrelated to those entities specifically identified. Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally. As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible. One with skill in the art will appreciate that the present invention is not limited in its application to the details of construction, the arrangements of components, category selections, weightings, predetermined signal limits, or the steps set forth in the description or drawings herein. The invention is capable of other embodiments and of being practiced or being carried out in many different ways. The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, 4$^{th}$ edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

What is claimed is:

1. A method for assaying a targeted cell and a non-cell analyte in a sample, comprising:
   (a) obtaining two plates facing each other and separated by a gap, wherein each of the plates has a sample contact area for contacting a sample;
   (b) obtaining a cell staining reagent, a capture agent, and a sample that contains or is suspected of containing a targeted cell and a non-cell analyte;
   (c) confining the cell staining reagent, and the capture agent, and the sample between the sample contact areas of the two plates, forming a thin sample layer, wherein, the sample has a thickness confined by the gap, wherein the cell staining reagent stains the targeted cell, and the capture agent specifically captures the non-cell analyte; and
   (d) imaging, after (c), the thin sample layer to (i) detect and count the targeted cell that is stained by the cell staining reagent, and (ii) detect the non-cell analyte that is captured by the capture agent;
   wherein the gap has a size configured to make the targeted cell have a monolayer in the thin sample layer and wherein, in the monolayer, the targeted cells do not have significant overlap.

2. The method of claim 1, wherein the capture agent is coated on one or both of the sample contact areas.

3. The method of claim 1, wherein the staining agent is coated on one or both of the sample contact areas.

4. The method of claim 1, wherein the staining agent and the capture reagent are coated on one or both of the sample contact areas.

5. The method of claim 1, wherein the method is performed by a device comprising:
   (a) the two plates facing each other and separated by the gap; and
   (b) the cell staining reagent and/or capture agent, are coated in one or both of the sample contact area.

6. The method of claim 1, wherein the method is performed by a device comprising:
   (a) the two plates facing each other and separated by the gap;
   (b) a microstructure that is between the sample contact areas of the two plates; and
   (c) the cell staining reagent and/or capture agent coated either on the surface of the microstructure or in one or both of the sample contact area.

7. The method of claim 5, wherein the device further comprises an imager that takes one or more images of the sample layer for detecting and counting the blood cells, and detecting and/or quantifying the analyte.

8. The method of claim 1, further comprising placing a microstructure between the sample contact areas of the two plates.

9. The method of claim 1, further comprising detecting the non-cell analyte using a detection agent, wherein the detection agent binds specifically to the non-cell analyte captured by the capture agent.

10. The method of claim 5, wherein the device further comprises a detection agent, wherein the detection agent binds the non-cell analyte.

11. The method of claim 5, wherein the two plates are movable relative to each other, wherein the gap between the two plates are regulated by spacers, wherein at least one of the spacers is in the sample contact area.

12. The method of claim 1, wherein detecting the cells and detecting the non-cell analyte are accomplished within a time period of 100 second or less.

13. The method of claim 1, wherein the blood sample is whole blood.

14. The method of claim 1, wherein the targeted cell is a white blood cell.

15. The method of claim 1, wherein the non-cell analyte is an acute phase reactant.

16. The method of claim 1, wherein the non-cell analyte is an acute phase reactant that is at least one compound selected from CRP or SAA.

17. The method of claim 1, wherein the capture reagent is an antibody, a nucleic acid, or an aptamer.

18. The method of claim 1, wherein the target cell is a white blood cell, and the non-cell analyte is an acute phase reactant that is at least one compound selected from CRP or SAA.

19. The method of claim 9, wherein the capture or detection agents are a monoclonal antibody that binds to CRP or SAA.

20. The method of claim 6, wherein the microstructure is conjugated with antibody.

21. The method of claim 6, wherein the microstructure is a plurality of beads.

22. The method of claim 21, wherein the plurality of beads is made of polystyrene or silica.

23. The method of claim 21, wherein the plurality of bead has a diameter of 2 to 30 μm.

24. The method of claim 21, wherein each of the plurality of beads has a diameter of 10 μm.

25. The method of claim 9, wherein the detection reagent is an antibody.

26. The method of claim 25, wherein the antibody is a monoclonal antibody.

27. The method of claim 26, wherein the monoclonal antibody binds to a complex of the capture reagent and CRP, or a complex of the capture agent and SAA.

28. The method of claim 9, wherein the detection agent is labeled with a fluorescent label.

29. The method of claim 28, wherein the fluorescent label is FITC, rhodamine, or Cy5.

30. The method of claim 1, wherein the cell staining reagent is SYTO 9 or YOYO.

31. The method of claim 6, wherein the two plates comprise a first plate and a second plate, and the device further comprises a plurality of spacers fixed to at least one of the first plate and the second plate; and wherein the plurality of spacers have (i) a pillar shape, (ii) a substantially flat top surface, (iii) a substantially uniform height, and (iv) a constant inter-spacer distance, wherein the sample contact areas are configured to hold a sample that contains or is suspected of containing a first analyte and a second analyte, and wherein the sample contact areas further comprise: a detection reagent on the sample contact area, wherein the detection reagent is configured to be diffusible in the sample and bind to the complex.

32. The method of claim 31, wherein the plurality of spacers is fixed on the first plate.

33. The method of claim 32, wherein the plurality of spacers has a substantially uniform height of 5 to 30 μm.

34. The method of claim 32, wherein the plurality of spacers has a substantially uniform height of 10 μm.

35. The method of claim 32, wherein the device further comprises a protein stabilizer immobilized thereon.

36. The method of claim 1, wherein the step (d) is performed by a mobile device that comprises an imager configured to capture images of the sample, and for identifying and counting the blood cells, and detecting and quantifying the analyte.

37. The method of claim 36, wherein the mobile device further comprises an adaptor, wherein the adaptor is configured to accommodate the device and to position the sample in a field of view (FOV) of the imager when the adaptor is attached to the mobile device and be attachable to a mobile device.

38. The method of claim 37, wherein the adaptor has a light source capable of emitting a light with a wavelength of 400 to 700 nm.

39. The method of claim 37, wherein the adaptor has a light source capable of emitting a light with a wavelength of 650 nm.

40. The method of claim 37, wherein the adaptor has a light source capable of emitting a light with a wavelength of 450 nm.

41. The method of claim 36, wherein the mobile device is an iPhone.

42. The method of claim 31, wherein the thickness of one of the plates times the Young's modulus of the one of the plate is in the range 60 to 750 GPa-um.

43. The method of claim 31, wherein, one of the two plates is a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3/GPa$.

44. The method of claim 31, wherein: the sample is a whole blood without liquid dilution; the spacers have a uniform height selected from 20 um to 30 um; one of the two plates is a flexible plate, the fourth power of the inter-spacer-distance (IDS) divided by the thickness (h) and the Young's modulus (E) of the flexible plate ($ISD^4/(hE)$) is $5\times10^6$ $um^3/GPa$ or less; and the thickness of the flexible plate times the Young's modulus of the flexible plate is in the range of 60 to 750 GPa-um.

45. The method of claim 31, wherein the spacers have a pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein one of the plates is a flexible plate, the fourth power of the inter-spacer distance (ISD) divided by the thickness (h) and the Young's modulus (E) of the flexible plate ($ISD^4/(hE)$) is $5\times10^6$ $um^3/GPa$ or less; and the thickness of the flexible plate times the Young's modulus of the flexible plate is in the range of 60 to 750 GPa-um.

46. The method of claim 1, wherein after the confining of the sample, the sample is imaged without any wash step.

47. The method of claim 1, wherein the capture agent comprises a detection agent.

48. The method of claim 1, wherein the diameter of beads equal or smaller than the spacer height.

\* \* \* \* \*